United States Patent [19]
Carson et al.

[11] Patent Number: 5,639,625
[45] Date of Patent: Jun. 17, 1997

[54] METHOD FOR DETECTING ANTIBODIES TO THROMBOMODULIN IN PATIENTS

[75] Inventors: Craig W. Carson, Edmond; Charles T. Esmon, Oklahoma City, both of Okla.

[73] Assignee: Oklahoma Medical Research Foundation, Oklahoma City, Okla.

[21] Appl. No.: 312,870

[22] Filed: Sep. 26, 1994

[51] Int. Cl.$^6$ .................................................. G01N 33/53
[52] U.S. Cl. ................. 435/7.92; 435/7.21; 435/7.93; 435/7.94; 435/7.95; 435/13; 435/961; 435/962; 435/967; 435/968; 436/531; 436/69; 536/27.1; 536/28.1; 536/29.1; 530/386; 530/387.9; 530/389.1; 530/389.3
[58] Field of Search ................. 435/7.21, 7.92–7.95, 435/13, 961, 962, 967, 968; 436/531, 69; 536/27.1, 28.1, 29.1; 530/386, 387.9, 389.1, 389.3

[56] References Cited

U.S. PATENT DOCUMENTS 4,912,207  3/1990  Majerus et al. ........................ 536/27

FOREIGN PATENT DOCUMENTS 0412841  2/1991  European Pat. Off. ........ C12P 21/02

OTHER PUBLICATIONS

Branch et al., "The demonstration of lupus anticoagulant by an enzyme-linked immunoadsorbent assay," *Clinical Immunology and Immunopathology* 39:298–307 (1986).

Brisson, et al., "Antibodies to thrombomodulin induce receptor-mediated endocytosis in human saphenous vein endothelial cells," *Thrombosis and Haemostasis* 68:737–743 (1992).

Cariou, et al., "Inhibition of Protein C activation by endothelial cells in the presence of lupus anticoagulant," *New England J Med* 314:1193–1194 (1986).

Cariou, et al., "Effect of lupus anticoagulant on antithrombogenic properties of endothelial cells–inhibition of thrombomodulin–dependent Protein C activation," *Thrombosis and Haemostasis* 60:54–58 (1988).

Dreyfus, et al., "Treatment of homozygous Protein C deficiency and neonatal purpura fulminans with a purified Protein C concentrate," *New England J Med* 325:1656–1568 (1991).

Esmon, C. T. "The regulation of natural anticoagulant pathways," *Science* 235:1348–1352 (1987).

Espevik, et al., "Inhibition of cytokine production by cyclosporin A and transforming growth factor β," *J. Exp Med* 166:571–576 (1987).

Freyssinet, et al., "An IgM lupus anticoagulant that neutralizes the enhancing effect of phospholipid on purified endothelial thrombomodulin activity–a mechanism for thrombosis," *Thrombosis & Haemostasis* 55:309–313 (1986).

Freyssinet, et al., "The effect of phospholipids on the activation of protein C by the human thrombinthrombomodulin complex," *Biochem J* 238:151–157 (1986).

Gibson, et al., "Autoantibodies to thrombomodulin: development of an enzyme immunoassay and a survey of their frequency in patients with the lupus anticoagulant," *Thrombosis and Haemostasis* 67:507–509 (1992).

(List continued on next page.)

*Primary Examiner*—Carol A. Spiegel
*Attorney, Agent, or Firm*—Sidley & Austin

[57] ABSTRACT

A novel method of detecting antibodies to thrombomodulin in plasma or serum as an indication of an individual's propensity to thrombosis or inflammation is disclosed. A method for identifiying patients at risks of thrombosis or glomerular nephritis by monitoring autoantibodies to truncated soluble thrombomodulin is revealed. A preferred method is an ELISA assay to detect antibodies to thrombomodulin.

19 Claims, 7 Drawing Sheets

Antibodies to Thrombomodulin
"Normals" vs "Unexplained Thrombosis"

OTHER PUBLICATIONS

Jackman, et al., "Human thrombomodulin gene is intron depleted: nucleic acid sequences of the cDNA and gene predict protein structure and suggest sites of regulatory control," *Proc Natl Acad Sci USA* 84:6425–6429 (1987).

Koyama, et al., "Relationship between post-translational glycosylation and anticoagulant function of secretable recombinant mutants of human thrombomodulin," *Br J Haematol* 78:515–522 (1991).

Love, P.E. and Santoro, S.A. "Antiphospholipid antibodies: anticardiolipin and the lupus anticoagulant in systemic lupus erythematosus (SLE) and in non–SLE disorders," *Annals of Internal Med* 112:682–698 (1990).

McCrae, et al., "Detection of endothelial cell–reactive immunoglobulin in patients with anti–phospholipid antibodies," *Br J Haematol* 79:596;605 (1991).

Oosting, et al., "In vitro studies of antiphospholipid antibodies and it cofactor, $\beta_2$–glycoprotein I, show negligible effects on endothelial cell mediated protein C activation," *Thrombosis & Haemostasis* 66:666–671 (1991).

Oosting, et al., "Autoantibodies directed against the epidermal growth factor–like domains of thrombomodulin inhibit protein C activation in vitro," *Br J Haematol* 85:761–768 (1993).

Pengo, et al., "Immunological specificity and mechanism of action of IgG lupus anticoagulants," *Blood* 70:69–76 (1987).

Potzsch, et al., "Thrombophilia in patients with lupus anticoagulant correlates with impaired anticoagulant activity of activated Protein C but not with decreased activation of Protein C," *Blood* 80(suppl):267a (1992). abstract No. 1059.

Rezaie, A.R. and Esmon, C. T., "The function of calcium in protein C activation by thrombin and the thrombinthrombomodulin complex can be distinguished by mutational analysis of protein C derivatives," *J. Biol. Chem* 267:26104–26109 (1992).

Ruiz–Arguelles, et al., "Acquired protein C deficiency in a patient with primary antiphospholipid syndrome. Relationship to reactivity of anticardiolipin antibody with thrombomodulin," *J Rheumatol* 16:381–383 (1989).

Suzuki, et al., "Structure and expression of human thrombomodulin, a thrombin receptor on endothelium acting as a cofactor for protein c activation," *EMBO J* 67:1891–1897 (1987).

Taylor, et al., "Protein C prevents the coagulopathic and lethal effects of *Escherichia coli* infusion in the baboon," *J Clin Invest* 79:918–925 (1987).

Thiagarajan, et al., "Monoclonal immunoglobulin M coagulation inhibitor with phospholipid specificity," *J. Clin Invest* 66:397–405 (1980).

Triplett, et al., "The relationship between lupus anticoagulants and antibodies to phospholipid," *JAMA* 259:550–554 (1988).

Triplett, et al., "The laboratory heterogeneity of lupus anticoagulants," *Arch Pathol Lab Med* 109:946–951 (1985).

Tsakiris, et al., "Lupus anticoagulant–antiphospholipid antibodies and thrombophilia. Relation to protein C –protein S –thrombomodulin," *J. Rheumatology* 17:785–789 (1990).

Tsiang, et al., "Functional domains of membrane–bound human thrombomodulin. EGF–like domains four to six and the serine/threonine–rich domain are required for cofactor activity," *J Biol Chem* 267:6164–6170 (1992).

Zushi, et al., "The last three consecutive epidermal growth factor–like structures of human thrombomodulin comprise the minimum functional domain for protein C–activating cofactor activity and anticoagulant activity," *J Biol Chem* 264:10351–10353 (1989).

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 575 amino acids
( B ) TYPE: amino acid
( D ) TOPOLOGY: linear ( i i ) MOLECULE TYPE: protein ( v ) FRAGMENT TYPE: N-terminal ( v i ) ORIGINAL SOURCE:
( A ) ORGANISM: Homo sapiens ( i x ) FEATURE:
( A ) NAME/KEY: Protein
( B ) LOCATION: 19..575

( x i ) SEQUENCE DESCRIPTION: SEQ ID NO:1:

| Met | Leu | Gly | Val | Leu | Val | Leu | Gly | Ala | Leu | Ala | Leu | Ala | Gly | Leu | Gly |
|---|---|---|---|---|---|---|---|---|---|---|---|---|---|---|---|
| | | | -15 | | | | | -10 | | | | | -5 | | |
| Phe | Pro | Ala | Pro | Ala | Glu | Pro | Gln | Pro | Gly | Gly | Ser | Gln | Cys | Val | Glu |
| | | 1 | | | 5 | | | | | | 10 | | | | |
| His | Asp | Cys | Phe | Ala | Leu | Tyr | Pro | Gly | Pro | Ala | Thr | Phe | Leu | Asn | Ala |
| 15 | | | | | 20 | | | | | 25 | | | | | 30 |
| Ser | Gln | Ile | Cys | Asp | Gly | Leu | Arg | Gly | His | Leu | Met | Thr | Val | Arg | Ser |
| | | | | 35 | | | | | 40 | | | | | 45 | |
| Ser | Val | Ala | Ala | Asp | Val | Ile | Ser | Leu | Leu | Leu | Asn | Gly | Asp | Gly | Gly |
| | | | 50 | | | | | 55 | | | | | 60 | | |
| Val | Gly | Arg | Arg | Arg | Leu | Trp | Ile | Gly | Leu | Gln | Leu | Pro | Pro | Gly | Cys |
| | | 65 | | | | | 70 | | | | | 75 | | | |
| Gly | Asp | Pro | Lys | Arg | Leu | Gly | Pro | Leu | Arg | Gly | Phe | Gln | Trp | Val | Thr |
| | 80 | | | | | 85 | | | | | 90 | | | | |
| Gly | Asp | Asn | Asn | Thr | Ser | Tyr | Ser | Arg | Trp | Ala | Arg | Leu | Asp | Leu | Asn |
| 95 | | | | | 100 | | | | | 105 | | | | | 110 |
| Gly | Ala | Pro | Leu | Cys | Gly | Pro | Leu | Cys | Val | Ala | Val | Ser | Ala | Ala | Glu |
| | | | | 115 | | | | | 120 | | | | | 125 | |
| Ala | Thr | Val | Pro | Ser | Glu | Pro | Ile | Trp | Glu | Glu | Gln | Gln | Cys | Glu | Val |
| | | | 130 | | | | | 135 | | | | | 140 | | |
| Lys | Ala | Asp | Gly | Phe | Leu | Cys | Glu | Phe | His | Phe | Pro | Ala | Thr | Cys | Arg |
| | | 145 | | | | | 150 | | | | | 155 | | | |
| Pro | Leu | Ala | Val | Glu | Pro | Gly | Ala | Ala | Ala | Ala | Val | Ser | Ile | Thr |
| | 160 | | | | | 165 | | | | | 170 | | | | |
| Tyr | Gly | Thr | Pro | Phe | Ala | Ala | Arg | Gly | Ala | Asp | Phe | Gln | Ala | Leu | Pro |
| 175 | | | | | 180 | | | | | 185 | | | | | 190 |
| Val | Gly | Ser | Ser | Ala | Ala | Val | Ala | Pro | Leu | Gly | Leu | Gln | Leu | Met | Cys |
| | | | | 195 | | | | | 200 | | | | | 205 | |
| Thr | Ala | Pro | Pro | Gly | Ala | Val | Gln | Gly | His | Trp | Ala | Arg | Glu | Ala | Pro |
| | | | 210 | | | | | 215 | | | | | 220 | | |
| Gly | Ala | Trp | Asp | Cys | Ser | Val | Glu | Asn | Gly | Gly | Cys | Glu | His | Ala | Cys |
| | | | 225 | | | | | 230 | | | | | 235 | | |
| Asn | Ala | Ile | Pro | Gly | Ala | Pro | Arg | Cys | Gln | Cys | Pro | Ala | Gly | Ala | Ala |
| | | 240 | | | | | 245 | | | | | 250 | | | |
| Leu | Gln | Ala | Asp | Gly | Arg | Ser | Cys | Thr | Ala | Ser | Ala | Thr | Gln | Ser | Cys |

```
        255                    260                   265                  270

Asn Asp Leu Cys Glu His Phe Cys Val Pro Asn Pro Asp Gln Pro Gly
                    275             280             285

Ser Tyr Ser Cys Met Cys Glu Thr Gly Tyr Arg Leu Ala Ala Asp Gln
                    290             295             300

His Arg Cys Glu Asp Val Asp Cys Ile Leu Glu Pro Ser Pro Cys
            305             310             315

Pro Gln Arg Cys Val Asn Thr Gln Gly Gly Phe Glu Cys His Cys Tyr
        320             325             330

Pro Asn Tyr Asp Leu Val Asp Gly Glu Cys Val Glu Pro Val Asp Pro
    335             340             345             350

Cys Phe Arg Ala Asn Cys Glu Tyr Gln Cys Gln Pro Leu Asn Gln Thr
                    355             360             365

Ser Tyr Leu Cys Val Cys Ala Glu Gly Phe Ala Pro Ile Pro His Glu
                    370             375             380

Pro His Arg Cys Gln Met Phe Cys Asn Gln Thr Ala Cys Pro Ala Asp
                385             390             395

Cys Asp Pro Asn Thr Gln Ala Ser Cys Glu Cys Pro Glu Gly Tyr Ile
        400             405             410

Leu Asp Asp Gly Phe Ile Cys Thr Asp Ile Asp Glu Cys Glu Asn Gly
    415             420             425             430

Gly Phe Cys Ser Gly Val Cys His Asn Leu Pro Gly Thr Phe Glu Cys
                    435             440             445

Ile Cys Gly Pro Asp Ser Ala Leu Ala Arg His Ile Gly Thr Asp Cys
                450             455             460

Asp Ser Gly Lys Val Asp Gly Gly Asp Ser Gly Ser Gly Glu Pro Pro
                465             470             475

Pro Ser Pro Thr Pro Gly Ser Thr Leu Thr Pro Pro Ala Val Gly Leu
                480             485             490

Val His Ser Gly Leu Leu Ile Gly Ile Ser Ile Ala Ser Leu Cys Leu
    495             500             505             510

Val Val Ala Leu Leu Ala Leu Leu Cys His Leu Arg Lys Lys Gln Gly
                    515             520             525

Ala Ala Arg Ala Lys Met Glu Tyr Lys Cys Ala Ala Pro Ser Lys Glu
                530             535             540

Val Val Leu Gln His Val Arg Thr Glu Arg Thr Pro Gln Arg Leu
                545             550             555
```

( 2 ) INFORMATION FOR SEQ ID NO:2:

( i ) SEQUENCE CHARACTERISTICS:
        ( A ) LENGTH: 1491 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens ( i x ) FEATURE:
        ( A ) NAME/KEY: CDS
        ( B ) LOCATION: 1..1491

( x i ) SEQUENCE DESCRIPTION: SEQ ID NO:2:

| | | | | | | | | | | | | | | | | |
|---|---|---|---|---|---|---|---|---|---|---|---|---|---|---|---|---|
| GCA | CCC | GCA | GAG | CCG | CAG | CCG | GGT | GGC | AGC | CAG | TGC | GTC | GAG | CAC | GAC | 48 |
| Ala | Pro | Ala | Glu | Pro | Gln | Pro | Gly | Gly | Ser | Gln | Cys | Val | Glu | His | Asp | |
| 1 | | | | 5 | | | | | 10 | | | | | 15 | | |
| TGC | TTC | GCG | CTC | TAC | CCG | GGC | CCC | GCG | ACC | TTC | CTC | AAT | GCC | AGT | CAG | 96 |
| Cys | Phe | Ala | Leu | Tyr | Pro | Gly | Pro | Ala | Thr | Phe | Leu | Asn | Ala | Ser | Gln | |
| | | | 20 | | | | | 25 | | | | | 30 | | | |
| ATC | TGC | GAC | GGA | CTG | CGG | GGC | CAC | CTA | ATG | ACA | GTG | CGC | TCC | TCG | GTG | 144 |
| Ile | Cys | Asp | Gly | Leu | Arg | Gly | His | Leu | Met | Thr | Val | Arg | Ser | Ser | Val | |
| | | 35 | | | | | 40 | | | | | 45 | | | | |
| GCT | GCC | GAT | GTC | ATT | TCC | TTG | CTA | CTG | AAC | GGC | GAC | GGC | GGC | GTT | GGC | 192 |
| Ala | Ala | Asp | Val | Ile | Ser | Leu | Leu | Leu | Asn | Gly | Asp | Gly | Gly | Val | Gly | |
| | 50 | | | | | 55 | | | | | 60 | | | | | |
| CGC | CGG | CGC | CTC | TGG | ATC | GGC | CTG | CAG | CTG | CCA | CCC | GGC | TGC | GGC | GAC | 240 |
| Arg | Arg | Arg | Leu | Trp | Ile | Gly | Leu | Gln | Leu | Pro | Pro | Gly | Cys | Gly | Asp | |
| 65 | | | | | 70 | | | | | 75 | | | | | 80 | |
| CCC | AAG | CGC | CTC | GGG | CCC | CTG | CGC | GGC | TTC | CAG | TGG | GTT | ACG | GGA | GAC | 288 |
| Pro | Lys | Arg | Leu | Gly | Pro | Leu | Arg | Gly | Phe | Gln | Trp | Val | Thr | Gly | Asp | |
| | | | | 85 | | | | | 90 | | | | | 95 | | |
| AAC | AAC | ACC | AGC | TAT | AGC | AGG | TGG | GCA | CGG | CTC | GAC | CTC | AAT | GGG | GCT | 336 |
| Asn | Asn | Thr | Ser | Tyr | Ser | Arg | Trp | Ala | Arg | Leu | Asp | Leu | Asn | Gly | Ala | |
| | | | 100 | | | | | 105 | | | | | 110 | | | |
| CCC | CTC | TGC | GGC | CCG | TTG | TGC | GTC | GCT | GTC | TCC | GCT | GCT | GAG | GCC | ACT | 384 |
| Pro | Leu | Cys | Gly | Pro | Leu | Cys | Val | Ala | Val | Ser | Ala | Ala | Glu | Ala | Thr | |
| | | 115 | | | | | 120 | | | | | 125 | | | | |
| GTG | CCC | AGC | GAG | CCG | ATC | TGG | GAG | GAG | CAG | CAG | TGC | GAA | GTG | AAG | GCC | 432 |
| Val | Pro | Ser | Glu | Pro | Ile | Trp | Glu | Glu | Gln | Gln | Cys | Glu | Val | Lys | Ala | |
| | 130 | | | | | 135 | | | | | 140 | | | | | |
| GAT | GGC | TTC | CTC | TGC | GAG | TTC | CAC | TTC | CCA | GCC | ACC | TGC | AGG | CCA | CTG | 480 |
| Asp | Gly | Phe | Leu | Cys | Glu | Phe | His | Phe | Pro | Ala | Thr | Cys | Arg | Pro | Leu | |
| 145 | | | | | 150 | | | | | 155 | | | | | 160 | |
| GCT | GTG | GAG | CCC | GGC | GCC | GCG | GCT | GCC | GCC | GTC | TCG | ATC | ACC | TAC | GGC | 528 |
| Ala | Val | Glu | Pro | Gly | Ala | Ala | Ala | Ala | Ala | Val | Ser | Ile | Thr | Tyr | Gly | |
| | | | | 165 | | | | | 170 | | | | | 175 | | |
| ACC | CCG | TTC | GCG | GCC | CGC | GGA | GCG | GAC | TTC | CAG | GCG | CTG | CCG | GTG | GGC | 576 |
| Thr | Pro | Phe | Ala | Ala | Arg | Gly | Ala | Asp | Phe | Gln | Ala | Leu | Pro | Val | Gly | |
| | | | 180 | | | | | 185 | | | | | 190 | | | |
| AGC | TCC | GCC | GCG | GTG | GCT | CCC | CTC | GGC | TTA | CAG | CTA | ATG | TGC | ACC | GCG | 624 |
| Ser | Ser | Ala | Ala | Val | Ala | Pro | Leu | Gly | Leu | Gln | Leu | Met | Cys | Thr | Ala | |
| | | 195 | | | | | 200 | | | | | 205 | | | | |
| CCG | CCC | GGA | GCG | GTC | CAG | GGG | CAC | TGG | GCC | AGG | GAG | GCG | CCG | GGC | GCT | 672 |
| Pro | Pro | Gly | Ala | Val | Gln | Gly | His | Trp | Ala | Arg | Glu | Ala | Pro | Gly | Ala | |
| | 210 | | | | | 215 | | | | | 220 | | | | | |
| TGG | GAC | TGC | AGC | GTG | GAG | AAC | GGC | GGC | TGC | GAG | CAC | GCG | TGC | AAT | GCG | 720 |
| Trp | Asp | Cys | Ser | Val | Glu | Asn | Gly | Gly | Cys | Glu | His | Ala | Cys | Asn | Ala | |
| 225 | | | | | 230 | | | | | 235 | | | | | 240 | |
| ATC | CCT | GGG | GCT | CCC | CGC | TGC | CAG | TGC | CCA | GCC | GGC | GCC | GCC | CTG | CAG | 768 |
| Ile | Pro | Gly | Ala | Pro | Arg | Cys | Gln | Cys | Pro | Ala | Gly | Ala | Ala | Leu | Gln | |
| | | | | 245 | | | | | 250 | | | | | 255 | | |
| GCA | GAC | GGG | CGC | TCC | TGC | ACC | GCA | TCC | GCG | ACG | CAG | TCC | TGC | AAC | GAC | 816 |
| Ala | Asp | Gly | Arg | Ser | Cys | Thr | Ala | Ser | Ala | Thr | Gln | Ser | Cys | Asn | Asp | |
| | | | 260 | | | | | 265 | | | | | 270 | | | |
| CTC | TGC | GAG | CAC | TTC | TGC | GTT | CCC | AAC | CCC | GAC | CAG | CCG | GGC | TCC | TAC | 864 |
| Leu | Cys | Glu | His | Phe | Cys | Val | Pro | Asn | Pro | Asp | Gln | Pro | Gly | Ser | Tyr | |
| | | 275 | | | | | 280 | | | | | 285 | | | | |
| TCG | TGC | ATG | TGC | GAG | ACC | GGC | TAC | CGG | CTG | GCG | GCC | GAC | CAA | CAC | CGG | 912 |
| Ser | Cys | Met | Cys | Glu | Thr | Gly | Tyr | Arg | Leu | Ala | Ala | Asp | Gln | His | Arg | |
| | 290 | | | | | 295 | | | | | 300 | | | | | |
| TGC | GAG | GAC | GTG | GAT | GAC | TGC | ATA | CTG | GAG | CCC | AGT | CCG | TGT | CCG | CAG | 960 |
| Cys | Glu | Asp | Val | Asp | Asp | Cys | Ile | Leu | Glu | Pro | Ser | Pro | Cys | Pro | Gln | |
| 305 | | | | | 310 | | | | | 315 | | | | | 320 | |

-continued

| | | | | | | | | | | | | | | | | |
|---|---|---|---|---|---|---|---|---|---|---|---|---|---|---|---|---|
| CGC | TGT | GTC | AAC | ACA | CAG | GGT | GGC | TTC | GAG | TGC | CAC | TGC | TAC | CCT | AAC | 1008 |
| Arg | Cys | Val | Asn | Thr 325 | Gln | Gly | Gly | Phe 330 | Glu | Cys | His | Cys | Tyr | Pro 335 | Asn | |
| TAC | GAC | CTG | GTG | GAC | GGC | GAG | TGT | GTG | GAG | CCC | GTG | GAC | CCG | TGC | TTC | 1056 |
| Tyr | Asp | Leu | Val 340 | Asp | Gly | Glu | Cys | Val 345 | Glu | Pro | Val | Asp 350 | Pro | Cys | Phe | |
| AGA | GCC | AAC | TGC | GAG | TAC | CAG | TGC | CAG | CCC | CTG | AAC | CAA | ACT | AGC | TAC | 1104 |
| Arg | Ala | Asn 355 | Cys | Glu | Tyr | Gln | Cys 360 | Gln | Pro | Leu | Asn | Gln 365 | Thr | Ser | Tyr | |
| CTC | TGC | GTC | TGC | GCC | GAG | GGC | TTC | GCG | CCC | ATT | CCC | CAC | GAG | CCG | CAC | 1152 |
| Leu | Cys 370 | Val | Cys | Ala | Glu | Gly 375 | Phe | Ala | Pro | Ile | Pro 380 | His | Glu | Pro | His | |
| AGG | TGC | CAG | ATG | TTT | TGC | AAC | CAG | ACT | GCC | TGT | CCA | GCC | GAC | TGC | GAC | 1200 |
| Arg 385 | Cys | Gln | Met | Phe | Cys 390 | Asn | Gln | Thr | Ala | Cys 395 | Pro | Ala | Asp | Cys | Asp 400 | |
| CCC | AAC | ACC | CAG | GCT | AGC | TGT | GAG | TGC | CCT | GAA | GGC | TAC | ATC | CTG | GAC | 1248 |
| Pro | Asn | Thr | Gln | Ala 405 | Ser | Cys | Glu | Cys | Pro 410 | Glu | Gly | Tyr | Ile | Leu 415 | Asp | |
| GAC | GGT | TTC | ATC | TGC | ACG | GAC | ATC | GAC | GAG | TGC | GAA | AAC | GGC | GGC | TTC | 1296 |
| Asp | Gly | Phe | Ile 420 | Cys | Thr | Asp | Ile | Asp 425 | Glu | Cys | Glu | Asn | Gly 430 | Gly | Phe | |
| TGC | TCC | GGG | GTG | TGC | CAC | AAC | CTC | CCC | GGT | ACC | TTC | GAG | TGC | ATC | TGC | 1344 |
| Cys | Ser | Gly 435 | Val | Cys | His | Asn | Leu 440 | Pro | Gly | Thr | Phe | Glu 445 | Cys | Ile | Cys | |
| GGG | CCC | GAC | TCG | GCC | CTT | GCC | CGC | CAC | ATT | GGC | ACC | GAC | TGT | GAC | TCC | 1392 |
| Gly | Pro 450 | Asp | Ser | Ala | Leu | Ala 455 | Arg | His | Ile | Gly | Thr 460 | Asp | Cys | Asp | Ser | |
| GGC | AAG | GTG | GAC | GGT | GGC | GAC | AGC | GGC | TCT | GGC | GAG | CCC | CCG | CCC | AGC | 1440 |
| Gly 465 | Lys | Val | Asp | Gly 470 | Gly | Asp | Ser | Gly | Ser 475 | Gly | Glu | Pro | Pro | Pro | Ser 480 | |
| CCG | ACG | CCC | GGC | TCC | ACC | TTG | ACT | CCT | CCG | GCC | GTG | GGG | CTC | GTG | CAT | 1488 |
| Pro | Thr | Pro | Gly | Ser 485 | Thr | Leu | Thr | Pro | Pro 490 | Ala | Val | Gly | Leu | Val 495 | His | |
| TCG | | | | | | | | | | | | | | | | 1491 |
| Ser | | | | | | | | | | | | | | | | |

( 2 ) INFORMATION FOR SEQ ID NO:3:

( i ) SEQUENCE CHARACTERISTICS:
        ( A ) LENGTH: 497 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| | | | | | | | | | | | | | | |
|---|---|---|---|---|---|---|---|---|---|---|---|---|---|---|
| Ala 1 | Pro | Ala | Glu | Pro 5 | Gln | Pro | Gly | Gly | Ser 10 | Gln | Cys | Val | Glu | His Asp 15 |
| Cys | Phe | Ala | Leu | Tyr 20 | Pro | Gly | Pro | Ala | Thr 25 | Phe | Leu | Asn | Ala | Ser Gln 30 |
| Ile | Cys | Asp | Gly 35 | Leu | Arg | Gly | His | Leu 40 | Met | Thr | Val | Arg | Ser 45 | Ser Val |
| Ala | Ala 50 | Asp | Val | Ile | Ser | Leu 55 | Leu | Leu | Asn | Gly | Asp 60 | Gly | Gly | Val Gly |
| Arg 65 | Arg | Arg | Leu | Trp | Ile 70 | Gly | Leu | Gln | Leu | Pro 75 | Pro | Gly | Cys | Gly Asp 80 |
| Pro | Lys | Arg | Leu | Gly 85 | Pro | Leu | Arg | Gly | Phe 90 | Gln | Trp | Val | Thr | Gly Asp 95 |
| Asn | Asn | Thr | Ser | Tyr 100 | Ser | Arg | Trp | Ala | Arg 105 | Leu | Asp | Leu | Asn | Gly Ala 110 |

-continued

| Pro | Leu | Cys | Gly | Pro | Leu | Cys | Val | Ala | Val | Ser | Ala | Ala | Glu | Ala | Thr |
|  | | 115 | | | | 120 | | | | | 125 | | | | |

| Val | Pro | Ser | Glu | Pro | Ile | Trp | Glu | Glu | Gln | Gln | Cys | Glu | Val | Lys | Ala |
| | 130 | | | | | 135 | | | | | 140 | | | | |

| Asp | Gly | Phe | Leu | Cys | Glu | Phe | His | Phe | Pro | Ala | Thr | Cys | Arg | Pro | Leu |
| 145 | | | | | 150 | | | | | 155 | | | | | 160 |

| Ala | Val | Glu | Pro | Gly | Ala | Ala | Ala | Ala | Ala | Val | Ser | Ile | Thr | Tyr | Gly |
| | | | | 165 | | | | | 170 | | | | | 175 | |

| Thr | Pro | Phe | Ala | Ala | Arg | Gly | Ala | Asp | Phe | Gln | Ala | Leu | Pro | Val | Gly |
| | | | 180 | | | | | 185 | | | | | 190 | | |

| Ser | Ser | Ala | Ala | Val | Ala | Pro | Leu | Gly | Leu | Gln | Leu | Met | Cys | Thr | Ala |
| | | 195 | | | | | 200 | | | | | 205 | | | |

| Pro | Pro | Gly | Ala | Val | Gln | Gly | His | Trp | Ala | Arg | Glu | Ala | Pro | Gly | Ala |
| | 210 | | | | | 215 | | | | | 220 | | | | |

| Trp | Asp | Cys | Ser | Val | Glu | Asn | Gly | Gly | Cys | Glu | His | Ala | Cys | Asn | Ala |
| 225 | | | | | 230 | | | | | 235 | | | | | 240 |

| Ile | Pro | Gly | Ala | Pro | Arg | Cys | Gln | Cys | Pro | Ala | Gly | Ala | Ala | Leu | Gln |
| | | | | 245 | | | | | 250 | | | | | 255 | |

| Ala | Asp | Gly | Arg | Ser | Cys | Thr | Ala | Ser | Ala | Thr | Gln | Ser | Cys | Asn | Asp |
| | | | 260 | | | | | 265 | | | | | 270 | | |

| Leu | Cys | Glu | His | Phe | Cys | Val | Pro | Asn | Pro | Asp | Gln | Pro | Gly | Ser | Tyr |
| | | 275 | | | | | 280 | | | | | 285 | | | |

| Ser | Cys | Met | Cys | Glu | Thr | Gly | Tyr | Arg | Leu | Ala | Ala | Asp | Gln | His | Arg |
| | 290 | | | | | 295 | | | | | 300 | | | | |

| Cys | Glu | Asp | Val | Asp | Asp | Cys | Ile | Leu | Glu | Pro | Ser | Pro | Cys | Pro | Gln |
| 305 | | | | | 310 | | | | | 315 | | | | | 320 |

| Arg | Cys | Val | Asn | Thr | Gln | Gly | Gly | Phe | Glu | Cys | His | Cys | Tyr | Pro | Asn |
| | | | | 325 | | | | | 330 | | | | | 335 | |

| Tyr | Asp | Leu | Val | Asp | Gly | Glu | Cys | Val | Glu | Pro | Val | Asp | Pro | Cys | Phe |
| | | | 340 | | | | | 345 | | | | | 350 | | |

| Arg | Ala | Asn | Cys | Glu | Tyr | Gln | Cys | Gln | Pro | Leu | Asn | Gln | Thr | Ser | Tyr |
| | | 355 | | | | | 360 | | | | | 365 | | | |

| Leu | Cys | Val | Cys | Ala | Glu | Gly | Phe | Ala | Pro | Ile | Pro | His | Glu | Pro | His |
| | 370 | | | | | 375 | | | | | 380 | | | | |

| Arg | Cys | Gln | Met | Phe | Cys | Asn | Gln | Thr | Ala | Cys | Pro | Ala | Asp | Cys | Asp |
| 385 | | | | | 390 | | | | | 395 | | | | | 400 |

| Pro | Asn | Thr | Gln | Ala | Ser | Cys | Glu | Cys | Pro | Glu | Gly | Tyr | Ile | Leu | Asp |
| | | | | 405 | | | | | 410 | | | | | 415 | |

| Asp | Gly | Phe | Ile | Cys | Thr | Asp | Ile | Asp | Glu | Cys | Glu | Asn | Gly | Gly | Phe |
| | | | 420 | | | | | 425 | | | | | 430 | | |

| Cys | Ser | Gly | Val | Cys | His | Asn | Leu | Pro | Gly | Thr | Phe | Glu | Cys | Ile | Cys |
| | | 435 | | | | | 440 | | | | | 445 | | | |

| Gly | Pro | Asp | Ser | Ala | Leu | Ala | Arg | His | Ile | Gly | Thr | Asp | Cys | Asp | Ser |
| | 450 | | | | | 455 | | | | | 460 | | | | |

| Gly | Lys | Val | Asp | Gly | Gly | Asp | Ser | Gly | Ser | Gly | Glu | Pro | Pro | Pro | Ser |
| 465 | | | | | 470 | | | | | 475 | | | | | 480 |

| Pro | Thr | Pro | Gly | Ser | Thr | Leu | Thr | Pro | Pro | Ala | Val | Gly | Leu | Val | His |
| | | | | 485 | | | | | 490 | | | | | 495 | |

Ser ( 2 ) INFORMATION FOR SEQ ID NO:4:

( i ) SEQUENCE CHARACTERISTICS:
        ( A ) LENGTH: 645 base pairs
        ( B ) TYPE: nucleic acid ( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Homo sapiens ( i x ) FEATURE:
    ( A ) NAME/KEY: CDS
    ( B ) LOCATION: 1..645

( x i ) SEQUENCE DESCRIPTION: SEQ ID NO:4:

```
GCA CCC GCA GAG CCG CAG CCG GGT GGC AGC CAG TGC GTC GAG CAC GAC      48
Ala Pro Ala Glu Pro Gln Pro Gly Gly Ser Gln Cys Val Glu His Asp
 1               5                  10                  15

TGC TTC GCG CTC TAC CCG GGC CCC GCG ACC TTC CTC AAT GCC AGT CAG      96
Cys Phe Ala Leu Tyr Pro Gly Pro Ala Thr Phe Leu Asn Ala Ser Gln
             20                  25                  30

ATC TGC GAC GGA CTG CGG GGC CAC CTA ATG ACA GTG CGC TCC TCG GTG     144
Ile Cys Asp Gly Leu Arg Gly His Leu Met Thr Val Arg Ser Ser Val
         35                  40                  45

GCT GCC GAT GTC ATT TCC TTG CTA CTG AAC GGC GAC GGC GGC GTT GGC     192
Ala Ala Asp Val Ile Ser Leu Leu Leu Asn Gly Asp Gly Gly Val Gly
     50                  55                  60

CGC CGG CGC CTC TGG ATC GGC CTG CAG CTG CCA CCC GGC TGC GGC GAC     240
Arg Arg Arg Leu Trp Ile Gly Leu Gln Leu Pro Pro Gly Cys Gly Asp
 65                  70                  75                  80

CCC AAG CGC CTC GGG CCC CTG CGC GGC TTC CAG TGG GTT ACG GGA GAC     288
Pro Lys Arg Leu Gly Pro Leu Arg Gly Phe Gln Trp Val Thr Gly Asp
                 85                  90                  95

AAC AAC ACC AGC TAT AGC AGG TGG GCA CGG CTC GAC CTC AAT GGG GCT     336
Asn Asn Thr Ser Tyr Ser Arg Trp Ala Arg Leu Asp Leu Asn Gly Ala
            100                 105                 110

CCC CTC TGC GGC CCG TTG TGC GTC GCT GTC TCC GCT GCT GAG GCC ACT     384
Pro Leu Cys Gly Pro Leu Cys Val Ala Val Ser Ala Ala Glu Ala Thr
        115                 120                 125

GTG CCC AGC GAG CCG ATC TGG GAG GAG CAG CAG TGC GAA GTG AAG GCC     432
Val Pro Ser Glu Pro Ile Trp Glu Glu Gln Gln Cys Glu Val Lys Ala
    130                 135                 140

GAT GGC TTC CTC TGC GAG TTC CAC TTC CCA GCC ACC TGC AGG CCA CTG     480
Asp Gly Phe Leu Cys Glu Phe His Phe Pro Ala Thr Cys Arg Pro Leu
145                 150                 155                 160

GCT GTG GAG CCC GGC GCC GCG GCT GCC GCC GTC TCG ATC ACC TAC GGC     528
Ala Val Glu Pro Gly Ala Ala Ala Ala Ala Val Ser Ile Thr Tyr Gly
                165                 170                 175

ACC CCG TTC GCG GCC CGC GGA GCG GAC TTC CAG GCG CTG CCG GTG GGC     576
Thr Pro Phe Ala Ala Arg Gly Ala Asp Phe Gln Ala Leu Pro Val Gly
            180                 185                 190

AGC TCC GCC GCG GTG GCT CCC CTC GGC TTA CAG CTA ATG TGC ACC GCG     624
Ser Ser Ala Ala Val Ala Pro Leu Gly Leu Gln Leu Met Cys Thr Ala
        195                 200                 205

CCG CCC GGA GCG GTC CAG GGG                                         645
Pro Pro Gly Ala Val Gln Gly
    210                 215
```

( 2 ) INFORMATION FOR SEQ ID NO:5:

( i ) SEQUENCE CHARACTERISTICS:
        ( A ) LENGTH: 215 amino acids
        ( B ) TYPE: amino acid ( D ) TOPOLOGY: linear ( i i ) MOLECULE TYPE: protein ( x i ) SEQUENCE DESCRIPTION: SEQ ID NO:5:

| Ala | Pro | Ala | Glu | Pro | Gln | Pro | Gly | Gly | Ser | Gln | Cys | Val | Glu | His | Asp |
|---|---|---|---|---|---|---|---|---|---|---|---|---|---|---|---|
| 1 | | | | 5 | | | | | 10 | | | | | 15 | |

| Cys | Phe | Ala | Leu | Tyr | Pro | Gly | Pro | Ala | Thr | Phe | Leu | Asn | Ala | Ser | Gln |
|---|---|---|---|---|---|---|---|---|---|---|---|---|---|---|---|
| | | | 20 | | | | 25 | | | | | 30 | | | |

| Ile | Cys | Asp | Gly | Leu | Arg | Gly | His | Leu | Met | Thr | Val | Arg | Ser | Ser | Val |
|---|---|---|---|---|---|---|---|---|---|---|---|---|---|---|---|
| | | 35 | | | | | 40 | | | | | 45 | | | |

| Ala | Ala | Asp | Val | Ile | Ser | Leu | Leu | Asn | Gly | Asp | Gly | Gly | Val | Gly |
|---|---|---|---|---|---|---|---|---|---|---|---|---|---|---|
| | 50 | | | | | 55 | | | | | 60 | | | |

| Arg | Arg | Arg | Leu | Trp | Ile | Gly | Leu | Gln | Leu | Pro | Pro | Gly | Cys | Gly | Asp |
|---|---|---|---|---|---|---|---|---|---|---|---|---|---|---|---|
| 65 | | | | | 70 | | | | | 75 | | | | | 80 |

| Pro | Lys | Arg | Leu | Gly | Pro | Leu | Arg | Gly | Phe | Gln | Trp | Val | Thr | Gly | Asp |
|---|---|---|---|---|---|---|---|---|---|---|---|---|---|---|---|
| | | | | 85 | | | | | 90 | | | | | 95 | |

| Asn | Asn | Thr | Ser | Tyr | Ser | Arg | Trp | Ala | Arg | Leu | Asp | Leu | Asn | Gly | Ala |
|---|---|---|---|---|---|---|---|---|---|---|---|---|---|---|---|
| | | | 100 | | | | | 105 | | | | | 110 | | |

| Pro | Leu | Cys | Gly | Pro | Leu | Cys | Val | Ala | Val | Ser | Ala | Ala | Glu | Ala | Thr |
|---|---|---|---|---|---|---|---|---|---|---|---|---|---|---|---|
| | | 115 | | | | | 120 | | | | | 125 | | | |

| Val | Pro | Ser | Glu | Pro | Ile | Trp | Glu | Glu | Gln | Gln | Cys | Glu | Val | Lys | Ala |
|---|---|---|---|---|---|---|---|---|---|---|---|---|---|---|---|
| | 130 | | | | | 135 | | | | | 140 | | | | |

| Asp | Gly | Phe | Leu | Cys | Glu | Phe | His | Phe | Pro | Ala | Thr | Cys | Arg | Pro | Leu |
|---|---|---|---|---|---|---|---|---|---|---|---|---|---|---|---|
| 145 | | | | | 150 | | | | | 155 | | | | | 160 |

| Ala | Val | Glu | Pro | Gly | Ala | Ala | Ala | Ala | Val | Ser | Ile | Thr | Tyr | Gly |
|---|---|---|---|---|---|---|---|---|---|---|---|---|---|---|
| | | | | 165 | | | | | 170 | | | | 175 | |

| Thr | Pro | Phe | Ala | Ala | Arg | Gly | Ala | Asp | Phe | Gln | Ala | Leu | Pro | Val | Gly |
|---|---|---|---|---|---|---|---|---|---|---|---|---|---|---|---|
| | | | 180 | | | | | 185 | | | | | 190 | | |

| Ser | Ser | Ala | Ala | Val | Ala | Pro | Leu | Gly | Leu | Gln | Leu | Met | Cys | Thr | Ala |
|---|---|---|---|---|---|---|---|---|---|---|---|---|---|---|---|
| | | 195 | | | | | 200 | | | | | 205 | | | |

| Pro | Pro | Gly | Ala | Val | Gln | Gly |
|---|---|---|---|---|---|---|
| | 210 | | | | | 215 |

( 2 ) INFORMATION FOR SEQ ID NO:6:

( i ) SEQUENCE CHARACTERISTICS:
    ( A ) LENGTH: 825 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Homo sapiens ( i x ) FEATURE:
    ( A ) NAME/KEY: CDS
    ( B ) LOCATION: 1..825

( x i ) SEQUENCE DESCRIPTION: SEQ ID NO:6:

| GGC | GCT | TGG | GAC | TGC | AGC | GTG | GAG | AAC | GGC | GGC | TGC | GAG | CAC | GCG | TGC | 48 |
|---|---|---|---|---|---|---|---|---|---|---|---|---|---|---|---|---|
| Gly | Ala | Trp | Asp | Cys | Ser | Val | Glu | Asn | Gly | Gly | Cys | Glu | His | Ala | Cys | |
| 1 | | | | 5 | | | | | 10 | | | | | 15 | | |

| AAT | GCG | ATC | CCT | GGG | GCT | CCC | CGC | TGC | CAG | TGC | CCA | GCC | GGC | GCC | GCC | 96 |
|---|---|---|---|---|---|---|---|---|---|---|---|---|---|---|---|---|
| Asn | Ala | Ile | Pro | Gly | Ala | Pro | Arg | Cys | Gln | Cys | Pro | Ala | Gly | Ala | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| CTG | CAG | GCA | GAC | GGG | CGC | TCC | TGC | ACC | GCA | TCC | GCG | ACG | CAG | TCC | TGC | 144 |
| Leu | Gln | Ala | Asp | Gly | Arg | Ser | Cys | Thr | Ala | Ser | Ala | Thr | Gln | Ser | Cys | |
| | | 35 | | | | | 40 | | | | | 45 | | | | |
| AAC | GAC | CTC | TGC | GAG | CAC | TTC | TGC | GTT | CCC | AAC | CCC | GAC | CAG | CCG | GGC | 192 |
| Asn | Asp | Leu | Cys | Glu | His | Phe | Cys | Val | Pro | Asn | Pro | Asp | Gln | Pro | Gly | |
| | 50 | | | | | 55 | | | | | 60 | | | | | |
| TCC | TAC | TCG | TGC | ATG | TGC | GAG | ACC | GGC | TAC | CGG | CTG | GCG | GCC | GAC | CAA | 240 |
| Ser | Tyr | Ser | Cys | Met | Cys | Glu | Thr | Gly | Tyr | Arg | Leu | Ala | Ala | Asp | Gln | |
| 65 | | | | 70 | | | | | 75 | | | | | | 80 | |
| CAC | CGG | TGC | GAG | GAC | GTG | GAT | GAC | TGC | ATA | CTG | GAG | CCC | AGT | CCG | TGT | 288 |
| His | Arg | Cys | Glu | Asp | Val | Asp | Asp | Cys | Ile | Leu | Glu | Pro | Ser | Pro | Cys | |
| | | | | 85 | | | | | 90 | | | | | 95 | | |
| CCG | CAG | CGC | TGT | GTC | AAC | ACA | CAG | GGT | GGC | TTC | GAG | TGC | CAC | TGC | TAC | 336 |
| Pro | Gln | Arg | Cys | Val | Asn | Thr | Gln | Gly | Gly | Phe | Glu | Cys | His | Cys | Tyr | |
| | | | 100 | | | | | 105 | | | | | 110 | | | |
| CCT | AAC | TAC | GAC | CTG | GTG | GAC | GGC | GAG | TGT | GTG | GAG | CCC | GTG | GAC | CCG | 384 |
| Pro | Asn | Tyr | Asp | Leu | Val | Asp | Gly | Glu | Cys | Val | Glu | Pro | Val | Asp | Pro | |
| | | 115 | | | | | 120 | | | | | 125 | | | | |
| TGC | TTC | AGA | GCC | AAC | TGC | GAG | TAC | CAG | TGC | CAG | CCC | CTG | AAC | CAA | ACT | 432 |
| Cys | Phe | Arg | Ala | Asn | Cys | Glu | Tyr | Gln | Cys | Gln | Pro | Leu | Asn | Gln | Thr | |
| | 130 | | | | | 135 | | | | | 140 | | | | | |
| AGC | TAC | CTC | TGC | GTC | TGC | GCC | GAG | GGC | TTC | GCG | CCC | ATT | CCC | CAC | GAG | 480 |
| Ser | Tyr | Leu | Cys | Val | Cys | Ala | Glu | Gly | Phe | Ala | Pro | Ile | Pro | His | Glu | |
| 145 | | | | 150 | | | | | 155 | | | | | | 160 | |
| CCG | CAC | AGG | TGC | CAG | ATG | TTT | TGC | AAC | CAG | ACT | GCC | TGT | CCA | GCC | GAC | 528 |
| Pro | His | Arg | Cys | Gln | Met | Phe | Cys | Asn | Gln | Thr | Ala | Cys | Pro | Ala | Asp | |
| | | | | 165 | | | | | 170 | | | | | 175 | | |
| TGC | GAC | CCC | AAC | ACC | CAG | GCT | AGC | TGT | GAG | TGC | CCT | GAA | GGC | TAC | ATC | 576 |
| Cys | Asp | Pro | Asn | Thr | Gln | Ala | Ser | Cys | Glu | Cys | Pro | Glu | Gly | Tyr | Ile | |
| | | | 180 | | | | | 185 | | | | | 190 | | | |
| CTG | GAC | GAC | GGT | TTC | ATC | TGC | ACG | GAC | ATC | GAC | GAG | TGC | GAA | AAC | GGC | 624 |
| Leu | Asp | Asp | Gly | Phe | Ile | Cys | Thr | Asp | Ile | Asp | Glu | Cys | Glu | Asn | Gly | |
| | | 195 | | | | | 200 | | | | | 205 | | | | |
| GGC | TTC | TGC | TCC | GGG | GTG | TGC | CAC | AAC | CTC | CCC | GGT | ACC | TTC | GAG | TGC | 672 |
| Gly | Phe | Cys | Ser | Gly | Val | Cys | His | Asn | Leu | Pro | Gly | Thr | Phe | Glu | Cys | |
| | 210 | | | | | 215 | | | | | 220 | | | | | |
| ATC | TGC | GGG | CCC | GAC | TCG | GCC | CTT | GCC | CGC | CAC | ATT | GGC | ACC | GAC | TGT | 720 |
| Ile | Cys | Gly | Pro | Asp | Ser | Ala | Leu | Ala | Arg | His | Ile | Gly | Thr | Asp | Cys | |
| 225 | | | | 230 | | | | | 235 | | | | | | 240 | |
| GAC | TCC | GGC | AAG | GTG | GAC | GGT | GGC | GAC | AGC | GGC | TCT | GGC | GAG | CCC | CCG | 768 |
| Asp | Ser | Gly | Lys | Val | Asp | Gly | Gly | Asp | Ser | Gly | Ser | Gly | Glu | Pro | Pro | |
| | | | | 245 | | | | | 250 | | | | | 255 | | |
| CCC | AGC | CCG | ACG | CCC | GGC | TCC | ACC | TTG | ACT | CCT | CCG | GCC | GTG | GGG | CTC | 816 |
| Pro | Ser | Pro | Thr | Pro | Gly | Ser | Thr | Leu | Thr | Pro | Pro | Ala | Val | Gly | Leu | |
| | | | 260 | | | | | 265 | | | | | 270 | | | |
| GTG | CAT | TCG | | | | | | | | | | | | | | 825 |
| Val | His | Ser | | | | | | | | | | | | | | |
| | | 275 | | | | | | | | | | | | | | |

(2) INFORMATION FOR SEQ ID NO:7:

(i) SEQUENCE CHARACTERISTICS:
        (A) LENGTH: 275 amino acids
        (B) TYPE: amino acid
        (D) TOPOLOGY: linear (ii) MOLECULE TYPE: protein (xi) SEQUENCE DESCRIPTION: SEQ ID NO:7:

| | | | | | | | | | | | | | | |
|---|---|---|---|---|---|---|---|---|---|---|---|---|---|---|
| Gly | Ala | Trp | Asp | Cys | Ser | Val | Glu | Asn | Gly | Gly | Cys | Glu | His | Ala | Cys |
| 1 | | | | 5 | | | | | 10 | | | | | 15 | |
| Asn | Ala | Ile | Pro | Gly | Ala | Pro | Arg | Cys | Gln | Cys | Pro | Ala | Gly | Ala | Ala |

|       |       |       |       | 20    |       |       |       |       | 25    |       |       |       |       | 30    |       |
|-------|-------|-------|-------|-------|-------|-------|-------|-------|-------|-------|-------|-------|-------|-------|-------|
| Leu   | Gln   | Ala   | Asp   | Gly   | Arg   | Ser   | Cys   | Thr   | Ala   | Ser   | Ala   | Thr   | Gln   | Ser   | Cys   |
|       |       | 35    |       |       |       |       | 40    |       |       |       |       | 45    |       |       |       |
| Asn   | Asp   | Leu   | Cys   | Glu   | His   | Phe   | Cys   | Val   | Pro   | Asn   | Pro   | Asp   | Gln   | Pro   | Gly   |
|       | 50    |       |       |       |       | 55    |       |       |       |       | 60    |       |       |       |       |
| Ser   | Tyr   | Ser   | Cys   | Met   | Cys   | Glu   | Thr   | Gly   | Tyr   | Arg   | Leu   | Ala   | Ala   | Asp   | Gln   |
| 65    |       |       |       |       | 70    |       |       |       |       | 75    |       |       |       |       | 80    |
| His   | Arg   | Cys   | Glu   | Asp   | Val   | Asp   | Cys   | Ile   | Leu   | Glu   | Pro   | Ser   | Pro   | Cys   |       |
|       |       |       |       | 85    |       |       |       |       | 90    |       |       |       | 95    |       |       |
| Pro   | Gln   | Arg   | Cys   | Val   | Asn   | Thr   | Gln   | Gly   | Gly   | Phe   | Glu   | Cys   | His   | Cys   | Tyr   |
|       |       |       | 100   |       |       |       |       | 105   |       |       |       |       | 110   |       |       |
| Pro   | Asn   | Tyr   | Asp   | Leu   | Val   | Asp   | Gly   | Glu   | Cys   | Val   | Glu   | Pro   | Val   | Asp   | Pro   |
|       |       | 115   |       |       |       |       | 120   |       |       |       |       | 125   |       |       |       |
| Cys   | Phe   | Arg   | Ala   | Asn   | Cys   | Glu   | Tyr   | Gln   | Cys   | Gln   | Pro   | Leu   | Asn   | Gln   | Thr   |
|       | 130   |       |       |       |       | 135   |       |       |       |       | 140   |       |       |       |       |
| Ser   | Tyr   | Leu   | Cys   | Val   | Cys   | Ala   | Glu   | Gly   | Phe   | Ala   | Pro   | Ile   | Pro   | His   | Glu   |
| 145   |       |       |       |       | 150   |       |       |       |       | 155   |       |       |       |       | 160   |
| Pro   | His   | Arg   | Cys   | Gln   | Met   | Phe   | Cys   | Asn   | Gln   | Thr   | Ala   | Cys   | Pro   | Ala   | Asp   |
|       |       |       |       | 165   |       |       |       |       | 170   |       |       |       |       | 175   |       |
| Cys   | Asp   | Pro   | Asn   | Thr   | Gln   | Ala   | Ser   | Cys   | Glu   | Cys   | Pro   | Glu   | Gly   | Tyr   | Ile   |
|       |       |       | 180   |       |       |       |       | 185   |       |       |       |       | 190   |       |       |
| Leu   | Asp   | Asp   | Gly   | Phe   | Ile   | Cys   | Thr   | Asp   | Ile   | Asp   | Glu   | Cys   | Glu   | Asn   | Gly   |
|       |       | 195   |       |       |       |       | 200   |       |       |       |       | 205   |       |       |       |
| Gly   | Phe   | Cys   | Ser   | Gly   | Val   | Cys   | His   | Asn   | Leu   | Pro   | Gly   | Thr   | Phe   | Glu   | Cys   |
|       |       | 210   |       |       |       |       | 215   |       |       |       |       | 220   |       |       |       |
| Ile   | Cys   | Gly   | Pro   | Asp   | Ser   | Ala   | Leu   | Ala   | Arg   | His   | Ile   | Gly   | Thr   | Asp   | Cys   |
| 225   |       |       |       |       | 230   |       |       |       |       | 235   |       |       |       |       | 240   |
| Asp   | Ser   | Gly   | Lys   | Val   | Asp   | Gly   | Gly   | Asp   | Ser   | Gly   | Ser   | Gly   | Glu   | Pro   | Pro   |
|       |       |       |       | 245   |       |       |       |       | 250   |       |       |       |       | 255   |       |
| Pro   | Ser   | Pro   | Thr   | Pro   | Gly   | Ser   | Thr   | Leu   | Thr   | Pro   | Pro   | Ala   | Val   | Gly   | Leu   |
|       |       |       | 260   |       |       |       |       | 265   |       |       |       |       | 270   |       |       |
| Val   | His   | Ser   |       |       |       |       |       |       |       |       |       |       |       |       |       |
|       |       | 275   |       |       |       |       |       |       |       |       |       |       |       |       |       |

( 2 ) INFORMATION FOR SEQ ID NO:8:

( i ) SEQUENCE CHARACTERISTICS:
    ( A ) LENGTH: 345 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Homo sapiens ( i x ) FEATURE:
    ( A ) NAME/KEY: CDS
    ( B ) LOCATION: 1..345

( x i ) SEQUENCE DESCRIPTION: SEQ ID NO:8:

| GTG | GAC | CCG | TGC | TTC | AGA | GCC | AAC | TGC | GAG | TAC | CAG | TGC | CAG | CCC | CTG | 48 |
|-----|-----|-----|-----|-----|-----|-----|-----|-----|-----|-----|-----|-----|-----|-----|-----|----|
| Val | Asp | Pro | Cys | Phe | Arg | Ala | Asn | Cys | Glu | Tyr | Gln | Cys | Gln | Pro | Leu |    |
| 1   |     |     |     | 5   |     |     |     |     | 10  |     |     |     |     | 15  |     |    |

| AAC | CAA | ACT | AGC | TAC | CTC | TGC | GTC | TGC | GCC | GAG | GGC | TTC | GCG | CCC | ATT | 96 |
|-----|-----|-----|-----|-----|-----|-----|-----|-----|-----|-----|-----|-----|-----|-----|-----|----|
| Asn | Gln | Thr | Ser | Tyr | Leu | Cys | Val | Cys | Ala | Glu | Gly | Phe | Ala | Pro | Ile |    |

|  |  |  |  |  |  |  | 20 |  |  |  | 25 |  |  |  | 30 |  |  |  |
|---|---|---|---|---|---|---|---|---|---|---|---|---|---|---|---|---|---|---|
| CCC | CAC | GAG | CCG | CAC | AGG | TGC | CAG | ATG | TTT | TGC | AAC | CAG | ACT | GCC | TGT | | | 144 |
| Pro | His | Glu | Pro | His | Arg | Cys | Gln | Met | Phe | Cys | Asn | Gln | Thr | Ala | Cys | | | |
|  |  | 35 |  |  |  |  | 40 |  |  |  |  | 45 |  |  |  | | | |
| CCA | GCC | GAC | TGC | GAC | CCC | AAC | ACC | CAG | GCT | AGC | TGT | GAG | TGC | CCT | GAA | | | 192 |
| Pro | Ala | Asp | Cys | Asp | Pro | Asn | Thr | Gln | Ala | Ser | Cys | Glu | Cys | Pro | Glu | | | |
|  | 50 |  |  |  |  | 55 |  |  |  |  | 60 |  |  |  |  | | | |
| GGC | TAC | ATC | CTG | GAC | GAC | GGT | TTC | ATC | TGC | ACG | GAC | ATC | GAC | GAG | TGC | | | 240 |
| Gly | Tyr | Ile | Leu | Asp | Asp | Gly | Phe | Ile | Cys | Thr | Asp | Ile | Asp | Glu | Cys | | | |
| 65 |  |  |  |  | 70 |  |  |  |  | 75 |  |  |  |  | 80 | | | |
| GAA | AAC | GGC | GGC | TTC | TGC | TCC | GGG | GTG | TGC | CAC | AAC | CTC | CCC | GGT | ACC | | | 288 |
| Glu | Asn | Gly | Gly | Phe | Cys | Ser | Gly | Val | Cys | His | Asn | Leu | Pro | Gly | Thr | | | |
|  |  |  |  | 85 |  |  |  |  | 90 |  |  |  |  | 95 |  | | | |
| TTC | GAG | TGC | ATC | TGC | GGG | CCC | GAC | TCG | GCC | CTT | GCC | CGC | CAC | ATT | GGC | | | 336 |
| Phe | Glu | Cys | Ile | Cys | Gly | Pro | Asp | Ser | Ala | Leu | Ala | Arg | His | Ile | Gly | | | |
|  |  |  | 100 |  |  |  |  | 105 |  |  |  |  |  | 110 |  | | | |
| ACC | GAC | TGT |  |  |  |  |  |  |  |  |  |  |  |  |  | | | 345 |
| Thr | Asp | Cys |  |  |  |  |  |  |  |  |  |  |  |  |  | | | |
|  |  | 115 |  |  |  |  |  |  |  |  |  |  |  |  |  | | | |

( 2 ) INFORMATION FOR SEQ ID NO:9:

( i ) SEQUENCE CHARACTERISTICS:
        ( A ) LENGTH: 115 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| Val | Asp | Pro | Cys | Phe | Arg | Ala | Asn | Cys | Glu | Tyr | Gln | Cys | Gln | Pro | Leu |
|---|---|---|---|---|---|---|---|---|---|---|---|---|---|---|---|
| 1 |  |  |  | 5 |  |  |  |  | 10 |  |  |  |  | 15 |  |
| Asn | Gln | Thr | Ser | Tyr | Leu | Cys | Val | Cys | Ala | Glu | Gly | Phe | Ala | Pro | Ile |
|  |  |  | 20 |  |  |  |  | 25 |  |  |  |  | 30 |  |  |
| Pro | His | Glu | Pro | His | Arg | Cys | Gln | Met | Phe | Cys | Asn | Gln | Thr | Ala | Cys |
|  |  | 35 |  |  |  |  | 40 |  |  |  |  | 45 |  |  |  |
| Pro | Ala | Asp | Cys | Asp | Pro | Asn | Thr | Gln | Ala | Ser | Cys | Glu | Cys | Pro | Glu |
|  | 50 |  |  |  |  | 55 |  |  |  |  | 60 |  |  |  |  |
| Gly | Tyr | Ile | Leu | Asp | Asp | Gly | Phe | Ile | Cys | Thr | Asp | Ile | Asp | Glu | Cys |
| 65 |  |  |  |  | 70 |  |  |  |  | 75 |  |  |  |  | 80 |
| Glu | Asn | Gly | Gly | Phe | Cys | Ser | Gly | Val | Cys | His | Asn | Leu | Pro | Gly | Thr |
|  |  |  |  | 85 |  |  |  |  | 90 |  |  |  |  | 95 |  |
| Phe | Glu | Cys | Ile | Cys | Gly | Pro | Asp | Ser | Ala | Leu | Ala | Arg | His | Ile | Gly |
|  |  |  | 100 |  |  |  |  | 105 |  |  |  |  |  | 110 |  |
| Thr | Asp | Cys |  |  |  |  |  |  |  |  |  |  |  |  |  |
|  |  | 115 |  |  |  |  |  |  |  |  |  |  |  |  |  |

( 2 ) INFORMATION FOR SEQ ID NO:10:

( i ) SEQUENCE CHARACTERISTICS:
        ( A ) LENGTH: 105 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens -continued

```
( i x ) FEATURE:
        ( A ) NAME/KEY: CDS
        ( B ) LOCATION: 1..105

( x i ) SEQUENCE DESCRIPTION: SEQ ID NO:10:

GAC  TCC  GGC  AAG  GTG  GAC  GGT  GGC  GAC  AGC  GGC  TCT  GGC  GAG  CCC  CCG        48
Asp  Ser  Gly  Lys  Val  Asp  Gly  Gly  Asp  Ser  Gly  Ser  Gly  Glu  Pro  Pro
1                   5                        10                       15

CCC  AGC  CCG  ACG  CCC  GGC  TCC  ACC  TTG  ACT  CCT  CCG  GCC  GTG  GGG  CTC        96
Pro  Ser  Pro  Thr  Pro  Gly  Ser  Thr  Leu  Thr  Pro  Pro  Ala  Val  Gly  Leu
               20                       25                       30

GTG  CAT  TCG                                                                         105
Val  His  Ser
          35

( 2 ) INFORMATION FOR SEQ ID NO:11:

( i ) SEQUENCE CHARACTERISTICS:
                ( A ) LENGTH: 35 amino acids
                ( B ) TYPE: amino acid
                ( D ) TOPOLOGY: linear ( i i ) MOLECULE TYPE: protein ( x i ) SEQUENCE DESCRIPTION: SEQ ID NO:11:

Asp  Ser  Gly  Lys  Val  Asp  Gly  Gly  Asp  Ser  Gly  Ser  Gly  Glu  Pro  Pro
1                   5                        10                       15

Pro  Ser  Pro  Thr  Pro  Gly  Ser  Thr  Leu  Thr  Pro  Pro  Ala  Val  Gly  Leu
               20                       25                       30

Val  His  Ser
          35
```

METHOD FOR DETECTING ANTIBODIES TO THROMBOMODULIN IN PATIENTS

TECHNICAL FIELD OF THE INVENTION

The present invention relates the field of diagnosis of a patient's propensity for thrombotic disease and inflammation.

BACKGROUND OF THE INVENTION

Hemostasis is a natural process by which injured blood vessels are repaired through the combined activity of vascular, platelet, and plasma factors, counterbalanced by regulatory mechanisms which control the amount of activated platelets and fibrin at the site of injury. Vascular factors reduce blood flow to the injured blood vessels by local vasoconstriction and by compression of the blood vessels due to blood flow into the surrounding tissues. Hemostatic plugs to seal the damaged blood vessels are formed by activation of platelet adhesion followed by blood coagulation reactions leading to the formation of a fibrin clot. Hemostatic abnormalities can result in excessive bleeding or thrombosis. Activation of this coagulation cascade may contribute to inflammation.

In the blood coagulation pathway, serine protease proenzymes are activated, resulting in the formation of a prothrombin activator which is a complex of the enzyme Factor Xa, and cofactors Va and procoagulant phospholipid (anionic phospholipid present in plasma membranes of platelets, endothelial cells and erythrocytes). The prothrombin activator splits prothrombin into two parts, one of which is the enzyme thrombin. Thrombin then reacts with fibrinogen to form fibrin and also activates Factor XIII, an enzyme which catalyzes the formation of covalent bonds between fibrin molecules, resulting in the formation of a clot. Impairment of the blood coagulation pathway leads to excessive bleeding tendencies.

Regulatory mechanisms normally control activated coagulation, thus preventing the spread of local thrombosis or disseminated intravascular coagulation. One method of regulation involves the neutralization of enzymes and activated cofactors in the blood which are necessary for coagulation, e.g., Factors Va and VIIIa. In this process, thrombin binds to a receptor on the endothelial cell membrane called thrombomodulin. When bound to thrombomodulin, thrombin loses its ability to convert fibrinogen to fibrin and activates Protein C, a vitamin K-dependent serine protease enzyme. In the presence of Protein S (also a vitamin K-dependent protein) and phospholipid, activated Protein C catalyzes the proteolysis of Factors VIIIa and Va, destroying their cofactor function and subsequently terminating clot formation. Failure to activate Protein C may result in numerous thromboembolic manifestations and increased inflammation. Additionally, studies in the baboon *Papio cynocephalus cynocephalus* indicate that the Protein C pathway is critical in modulating the inflammatory and coagulopathic responses in vivo. (Taylor, et al., "Protein C prevents the coagulopathic and lethal effects of *Escherichia coli* infusion in the baboon," *J Clin Invest* 79:918–925 (1987)) Inhibition of Protein C activation by the thrombin-thrombomodulin complex leads to disruption of this regulatory pathway and uncontrolled coagulation, thrombosis, and inflammation. This concept is supported by the observation that patients with Protein C deficiency demonstrate thrombotic complications which are corrected by Protein C replacement therapy. (Esmon, "The regulation of natural anticoagulant pathways," *Science* 235:1348–1352 (1987); Dreyfus, et al., "Treatment of homozygous Protein C deficiency and neonatal purpura fulminans with a purified Protein C concentrate," *New Eng J of Med* 325:1565–1568 (1991))

Endogenous substances such as circulating anticoagulants (e.g., lupus coagulant) may affect blood coagulation. Lupus anticoagulant is a circulating anticoagulant which was first described in patients with systemic lupus erythematosus (SLE) and subsequently found associated with a wide variety of disorders. It is characterized as an immunoglobulin, or antibody, which reacts with anionic phospholipids and/or coagulation factors such as prothrombin used in in vitro coagulation assays such as PTT (partial thromboplastin time) and aPTT (activated partial thromboplastin time). The presence of lupus anticoagulant in the patient's plasma results in a prolonged PTT or aPTT which fails to correct with a 1:1 mixture of the patient's plasma and normal plasma.

Antiphospholipid antibodies have been found in plasma from many patients with lupus anticoagulant using an ELISA assay looking for antibodies which bind cardiolipin (Triplett, et al., "The relationship between lupus anticoagulants and antibodies to phospholipid," *JAMA* 259:550–554 (1988)) possibly in association with coagulation proteins or β-2-glycoprotein-1 (Pengo, et al., "Immunological specificity and mechanism of action of IgG lupus anticoagulants," *Blood* 70:69–76 (1987); Thiagarajan, et al., "Monoclonal immunoglobulin M: coagulation inhibitor with phospholipid specificity," *J Clin Invest* 66:397–405 (1980)).

Although the lupus anticoagulant inhibits the function of phospholipid and coagulation factors in in vitro coagulation assays, most patients with lupus anticoagulant do not bleed excessively, rather they have thrombosis. Paradoxically, patients with lupus anticoagulant demonstrate an increased risk of thrombosis, e.g., recurrent thromboembolism, myocardial infarction, stroke, thrombotic spontaneous abortion, and thrombocytopenia. However, not all patients with lupus anticoagulant have a propensity for thrombosis, and many patients suffering from unexplained thrombotic diseases do not test positively to lupus anticoagulant. Likewise, not all patients with SLE test positive for lupus anticoagulant and not all patients with lupus anticoagulant have SLE.

The pathogenesis of thrombosis associated with lupus anticoagulant has not been clearly elucidated. Extensive research has been conducted in an effort to explain the relationship between lupus anticoagulant and thrombotic episodes. Several investigators noted that antibodies from patients with lupus anticoagulant block the activation of Protein C by the thrombin-thrombomodulin complex. It has been proposed that these antibodies interfere with the phospholipid enhancement of Protein C activation by the thrombin-thrombomodulin complex. Cariou et al., "Inhibition of Protein C activation by endothelial cells in the presence of lupus anticoagulant," *New England J of Med* 314:1193–1194 (1986); Cariou et al., "Effect of lupus anticoagulant on antithrombogenic properties of endothelial cells-inhibition of thrombomodulin-dependent Protein C activation," *Thrombosis and Haemostasis* 60:54–58 (1988); Freyssinet, et al., "An IgM lupus anticoagulant that neutralizes the enhancing effect of phospholipid on purified endothelial thrombomodulin activity-a mechanism for thrombosis," *Thrombosis and Haemostasis* 55:309–313 (1986). This hypothesis is supported by the fact that added phospholipid neutralizes the ability of lupus anticoagulant immunoglobulin to inhibit thrombomodulin function. Cariou et al., "Effect of lupus anticoagulant on antithrombogenic properties of endothelial cells-inhibition of thrombomodulin-dependent Protein C activation," *Thrombosis and Haemostasis* 60:54–58 (1988); Freyssinet, et al., "The effect of phospholipids on the activation of protein C by the human thrombin-thrombomodulin complex," *Biochem J* 238:151–157 (1986); Freyssinet, et al., "An IgM lupus anticoagulant that neutralizes the enhancing effect of phospholipid on purified endothelial thrombomodulin activity—a mechanism for thrombosis," *Thrombosis and Haemostasis* 55:309–313 (1986). However, in some cases where antithrombomodulin activity has been identified in thrombomodulin-dependent Protein C activation assays, disparities have been found between the titer of antiphospholipid antibody and the amount of antithrombomodulin activity, suggesting that the mechanism of thrombosis may involve more than blocking phospholipids. Cariou, et al., "Effect of lupus anticoagulant on antithrombogenic properties of endothelial cells-inhibition of thrombomodulin-dependent protein C activation," *Thrombosis and Haemostasis* 60:54–58 (1988); Oosting, et al., "In vitro studies of antiphospholipid antibodies and its cofactor, β-glycoprotein I, show negligible effects on endothelial cell mediated Protein C activation," *Thrombosis and Haemostasis* 66:666–671 (1991); Triplett, et al., "The laboratory heterogeneity of lupus anticoagulants," *Arch Pathol Lab Med* 109:946–951 (1985); Tsakiris, et al., "Lupus anticoagulant—antiphospholipid antibodies and thrombophilia. Relation to Protein C—Protein S—thrombomodulin," *J Rheumatol* 17:785–789 (1990); Ruiz-Arguelles, et al., "Acquired protein C deficiency in a patient with primary antiphospholipid syndrome. Relationship to reactivity of anticardiolipin antibody with thrombomodulin," *J Rheumatol* 16:381–383 (1989).

Gibson et al attempted to demonstrate the direct binding of antibodies to thrombomodulin as a possible mechanism for blocking the activation of Protein C by the thrombin-thrombomodulin complex. Plasma from patients with lupus anticoagulant was examined for the presence of antibodies to thrombomodulin using an enzyme-linked immunosorbent assay (ELISA). In this assay, purified human placental thrombomodulin was coated to wells of a microtiter plate which was then probed with patient plasma. The results indicated that there was no significant antibody reactivity to thrombomodulin in patients with lupus anticoagulant when compared to lupus anticoagulant negative patients. The conclusion of the study was that antibodies to thrombomodulin do not exist. Gibson, et al., "Autoantibodies to thrombomodulin: development of an enzyme immanunoassay and a survey of their frequency in patients with the lupus anticoagulant," *Thrombosis and Haemostasis* 67:507–509 (1992).

Natural human thrombomodulin is a 75,000 kD endothelial cell protein having a structure which resembles the low density lipoprotein (LDL) receptor with an amino terminal lectin-like region followed by six tandem epidermal growth factor (EGF)-like repeats. The last three EGF-like repeats (EGF 456) contain the region required for thrombin binding and Protein C activation. Zushi, et al., "The last three consecutive epidermal growth factor-like structures of human thrombomodulin comprise the minimum functional domain for protein C—activating cofactor activity and anticoagulant activity," *J Biol Chem* 264:10351–10353 (1989); Tsiang, et al., "Functional domains of membrane-bound human thrombomodulin. EGF 456 domains and the serine/threonine-rich domain are required for cofactor activity," *J Biol Chem* 267:6164–6170 (1992). After the EGF-like repeats is a serine/threonine-rich region containing chondroitin sulfate, followed by a transmembrane domain and a short cytoplasmic tail. The basic amino acid structure of human thrombomodulin cDNA (SEQ ID NO:1) is presented sequentially in Suzuki, et al., "Structure and expression of human thrombomodulin, a thrombin receptor on endothelium acting as a cofactor for protein C activation," *EMBO J* 6:1891 (1987): signal peptide (16, 18, or 21 residues), amino-terminal lectin domain (223–226 residues), six EGF-like (epidermal growth factor) domains (236–240 residues), serine-threonin rich chondroitin sulfate domain (34–37 residues), transmembrane region (23–24 residues), and cytoplasmic domain (36–38 residues), for a total of 575 amino acid residues.

Oosting, et al. identified patient immunoglobulin fractions (IgG) which inhibited Protein C activation and was able to demonstrate by ELISA binding of these antibodies to the epidermal growth factors (EGF) domain in SLE patients with thrombotic complications. (Oosting, "Autoantibodies directed against the epidermal growth factor-like domains of thrombomodulin inhibit protein C activation in vitro," *British Journal of Haematology* 85:761–768 (1993). These authors concluded that autoantibodies to thrombomodulin must be directed specifically against the restricted region of thrombomodulin containing the epidermal growth factor (EGF) domain.

In contrast to the reports of the literature, it has now been found that antibodies to various regions of thrombomodulin exist, and an assay for detection of these antibodies has been developed as a diagnostic tool for patients having a propensity for unexplained thrombosis or inflammation whether or not they have lupus anticoagulant.

SUMMARY OF THE INVENTION

This invention concerns a method for testing patient plasma or serum for antibodies to thrombomodulin as an indication of a propensity for thrombotic disease or inflammation.

In another aspect, this invention concerns a method for testing patient plasma or serum to determine the patient's level of risk for thrombosis.

In yet another aspect, this invention concerns a method for monitoring a patient with lupus anticoagulant or thrombotic tendencies for thrombosis.

DETAILED DESCRIPTION OF THE INVENTION

Figure 1:
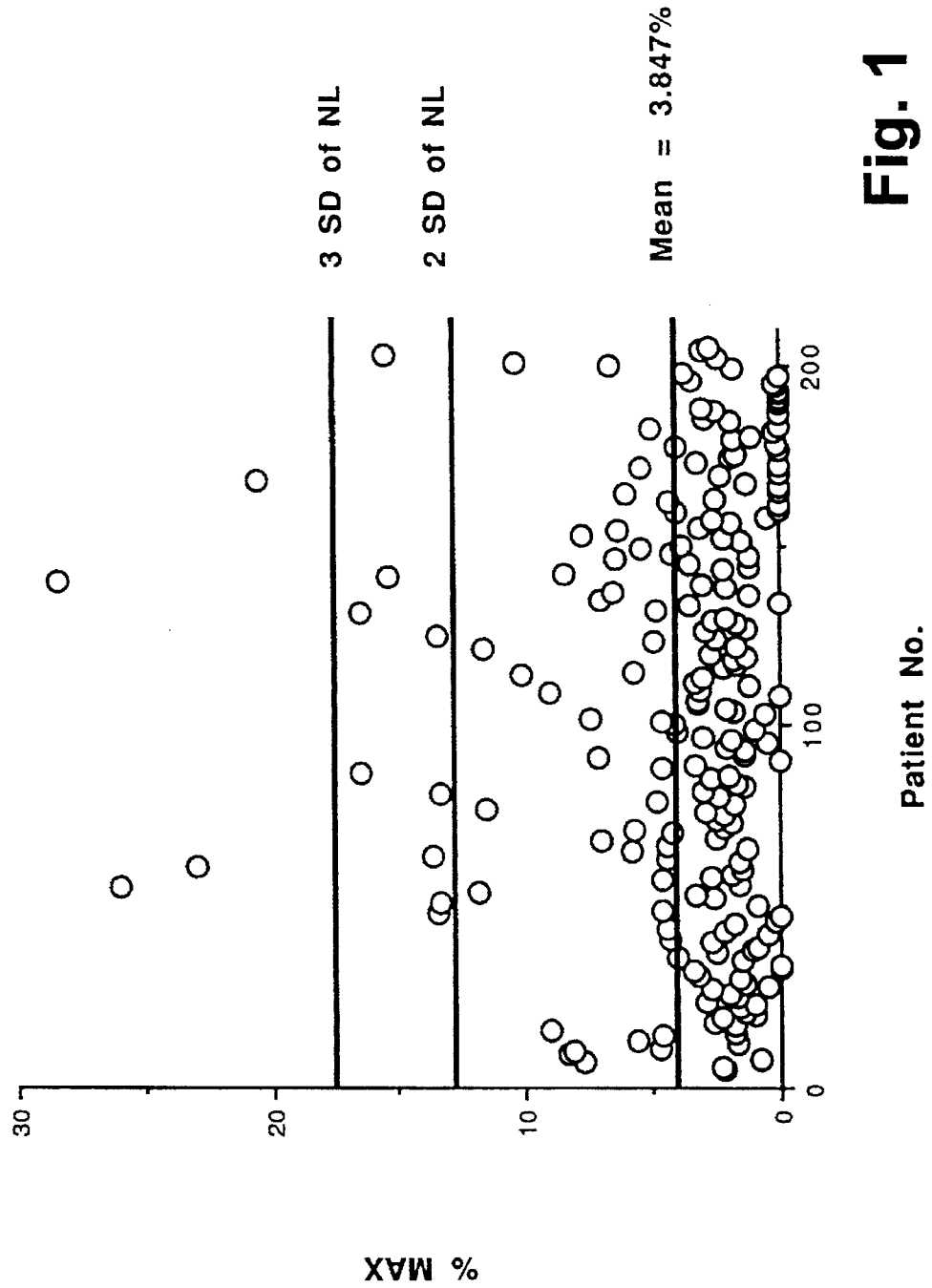
FIG. 1 is a graph depicting the results of the ELISA assays for detecting antibodies to thrombomodulin in normal donor plasma.

An enzyme-linked immunosorbent assay (ELISA) is disclosed which can be used to identify patients with antibodies to thrombomodulin.

In order to run the assay, it is necessary to obtain a truncated, soluble human thrombomodulin which essentially lacks the cytoplasmic and transmembrane domains of thrombomodulin, or at least one of several fragments of thrombomodulin. By "essentially lacks" it is meant that the sequence chosen may have a few of the amino acids normally associated with the transmembrane domain, but not so many that the thrombomodulin becomes insoluble. In the sequence of human thrombomodulin cDNA (SEQ ID NO:1) as published by Suzuki, et al., the cytoplasmic and transmembrane domains are identified as amino acid residues 497–575. (Suzuki, et al., "Structure and expression of human thrombomodulin, a thrombin receptor on endothelium acting as a cofactor for protein C activation," *EMBO J* 6:1891 (1987)) The truncated soluble human thrombomodulin or its fragments can be made using recombinant DNA techniques or using any known method of synthesizing or purifying protein.

The plasmid pUC18TM containing the entire nucleotide coding sequence for human thrombomodulin can be obtained from Eli Lilly and Company (Indianapolis, Ind.) via the Agricultural Research Culture Collection under Number NRRL-B18524 and utilized to make a suitable recombinant soluble human thrombomodulin. The nucleic acid sequence listing and characterization of this soluble human thrombomodulin is disclosed in European Patent Application No. 0 412 841, which is herein incorporated by reference. DNA constructs are then produced by the polymerase chain reaction using the plasmid pUC18TM as a template for the following human thrombomodulin fragments: a truncated, soluble form of thrombomodulin lacking the transmembrane and cytoplasmic domains ("soluble thrombomodulin" or "sTM") (SEQ ID NO:3); an amino terminal lectin domain ("TM-lectin" domain) (SEQ ID NO:5); an EGF 1-6 domain ("TM1-6" domain) (SEQ ID NO:7); an EGF 456 domain ("TM456" domain) (SEQ ID NO:9); and a serine/threonine rich chondroitin sulfate attachment domain ("TM-CS" domain) (SEQ ID NO:11). cDNA sequences for the full length fragments are given in SEQ ID NO:2, SEQ ID NO:4 (TM-lectin); SEQ ID NO:6 (TM1-6 domain); SEQ ID NO:8 (TM 456 domain) and SEQ ID NO:10; (TM-CS domain).

The desired form of thrombomodulin may be inserted into an appropriate expression vector, such as the RSV (rouse sarcoma virus) expression vector, and the vector transfected into human 293 cells for expression. The resultant protein is purified to homogeneity using anion exchange and thrombin affinity chromatography, described in detail in Example 9.

DNA constructs of the TM-lectin (SEQ ID NO:5), TM1-6 (SEQ ID NO:7), TM456 (SEQ ID NO:9), and TM-CS (SEQ ID NO:11) domains are preferably cloned into the RSV vector modified to add a 24 amino acid epitope for the calcium-dependent monoclonal antibody HPC-4 as described in Rezaie, et al., "The function of calcium in Protein C activation by thrombin and the thrombin-thrombomodulin complex can be distinguished by mutational analysis of Protein C derivatives," *J Biol Chem* 267:26104–26109 (1992), which is herein incorporated by reference. After the vector is transfected into human 293 cells and expressed, the resultant proteins are purified using HPC-4 affinity chromatography. A purification procedure is given in Example 10.

The purified recombinant human thrombomodulin (SEQ ID NO:3) and the four particular domains (SEQ ID NO:5, SEQ ID NO:7, SEQ ID NO:9, and SEQ ID NO:11) can each be incorporated as the plate-binding component of ELISA assays to detect antibodies to human thrombomodulin. The preferred plate-binding component of the ELISA assay for screening patient samples for antibodies to thrombomodulin is the soluble thrombomodulin (SEQ ID NO:3). However, antibodies to specific domains of thrombomodulin may correlate with specific disease manifestations. For example, antibodies to the EGF domains (SEQ ID NO:7 and SEQ ID NO:9) which inhibit Protein C activation may be associated with thrombosis, while antibodies to the lectin (SEQ ID NO:5) or chondroitin sulfate domains (SEQ ID NO:11) may be associated with other manifestations. Moreover, the antibody reactivity to these general domains may be further localized to smaller epitopes, which may also be used in the ELISA assay.

In the ELISA assay, protein fragment of interest such as the recombinant soluble thrombomodulin (SEQ ID NO:3), for example, is coated onto wells of a microtiter plate. A blocking buffer is applied to the wells to prevent subsequent nonspecific binding of the patient antibodies to the plastic wells. Dilute patient plasma or serum or purified IgG extracted from patient plasma or serum is added to microtiter wells and incubated overnight to allow only antibodies specific for sTM which may be present to bind to the sTM attached to the microtiter wells. After washing to remove all unbound antibodies, an enzyme linked anti-human antibody (E-Ab complex) is added to the microtiter wells such as alkaline phosphatase conjugated anti-human IgG. After incubation to allow the anti-human antibody of the E-Ab complex to specifically bind the patient sTM antibodies, the microtiter wells are washed again to remove all excess E-Ab complex. To determine the degree of specific antibody binding to sTM, a suitable substrate for the enzyme of the E-Ab complex is added to the microtiter wells. The enzyme-substrate reaction generates an end product with either color, fluorescent, chemiluminescent, or radioactive properties. The amount of end product measurable by color intensity or radioactivity is proportional to the amount of specific antibody binding. Examples of substrates include p-nitrophenyl phosphate for visual detection, methylumbelliferyl phosphate for fluorescent detection, and $^{125}$Iodine for radioactive detection. To one skilled in the art, it is apparent that there are a variety of other E-Ab complexes available for antibody detection which may include combinations of other enzymes and anti-human antibodies, and the invention is not limited to this example.

Reactivity of the patient sample is compared to standard reference antisera obtained from an individual with lupus anticoagulant. Results from the plate-binding ELISA can be analyzed in terms of percent (%) maximal binding as follows:

$$\% MAX = \frac{A_{sTM/patient} - A_{blank/patient}}{A_{sTM/max} - A_{blank/max}} \times 100$$

where $A_{sTM/patient}$ is the absorbance obtained from the microtiter well containing sTM and patient plasma; Ablank/patient, absorbance from the microtiter well containing only patient plasma; $A_{sTM/max}$, absorbance from the microtiter well containing sTM and standard reference antisera; and $A_{blank/max}$, absorbance from the microtiter well containing only standard reference antisera. $A_{sTM/max} - A_{blank/max}$ represents maximal reactivity of antibody to thrombomodulin (hereinafter referred to as "reference standard").

The plate-binding ELISA assay is to be utilized in screening patients with lupus, lupus anticoagulant, unexplained thrombosis, or similar diseases associated with thromboembolism or inflammation for the presence of antibodies to human thrombomodulin. The presence of these antibodies will be used to predict patients most at risk for thrombosis and/or inflammation.

EXAMPLE 1

ELISA Assay for Antibodies to Thrombomodulin Using Normal Donor Plasma

Recombinant soluble thrombomodulin (sTM) (SEQ ID NO:3) encoded by the cDNA construct given in SEQ ID NO:2 was suspended in a coating buffer (TBS) containing 0.15M NaCl and 0.02M Tris-HCl, pH 7.5, at a concentration of 10 μg/ml. About 50 μl of the sTM suspension was added to each well in every other row on a microtiter plate, and the plates were incubated overnight at 4° C., thus allowing the sTM to adhere to the plastic wells. After removal of the remaining fluid, the microtiter wells were washed twice with a wash buffer consisting of 0.15M NaCl, 0.02M Tris-HCl, pH 7.5, and 0.1% TWEEN 20(polyoxyethylensorbitan monolaurate). The microtiter wells were then filled once with 200 μl of blocking buffer (10% nonfat dry milk in TBS) to block non-specific binding and washed twice with the wash buffer.

Plasma samples were then applied to the microtiter plate at 50 μl/well as follows: 1) patient plasma diluted 1:100 in diluting buffer (2% nonfat dry milk in TBS) into an sTM well; 2) patient plasma diluted 1:100 in diluting buffer into a blank well; 3) standard reference antiserum obtained from a patient with lupus anticoagulant (hereinafter referred to as "max") diluted 1:100 with diluting buffer into an sTM well; and 4) standard reference antisera (max) control diluted 1:100 with diluting buffer into a blank well. The microtiter plate was incubated overnight at 4° C., giving antibodies present in the plasma the opportunity to bind to the sTM. After washing three times with wash buffer, about 50 μl of alkaline phosphatase conjugated goat anti-human IgG (or a mixture of IgG, IgM, and IgA) at 0.1 μg/ml in diluting buffer was applied to each well. Following a four hour incubation at room temperature, the microtiter wells were washed four times with wash buffer. About 50 μl of p-nitrophenyl phosphate substrate at 1 mg/ml in substrate buffer (100 mM diethanolamine, 5 mM $MgCl_2$, and 0.02% sodium azide) was applied to each microtiter well. After a thirty minute incubation for color development, the microtiter wells were analyzed for absorbance (A) at 405 mμ using a microtiter plate reader. Results were analyzed in terms of percent (%) maximal binding.

Using this assay, 201 normal blood donors were evaluated for antibody reactivity to the truncated recombinant thrombomodulin. As graphically depicted in FIG. 1, the average reactivity of normal donors was 3.85% compared to the reference standard. An arbitrary cut-off was set at 17.4% of the reference standard and represents three standard deviations of the normal, or a 98% confidence interval. Only 4 of the 201 normal donors had reactivity above the cut off value of 7.4%. There was no correlation between antibody to thrombomodulin reactivity and age, sex, height, weight, smoking status, pregnancy or use of oral contraceptives.

EXAMPLE 2

Figure 2:
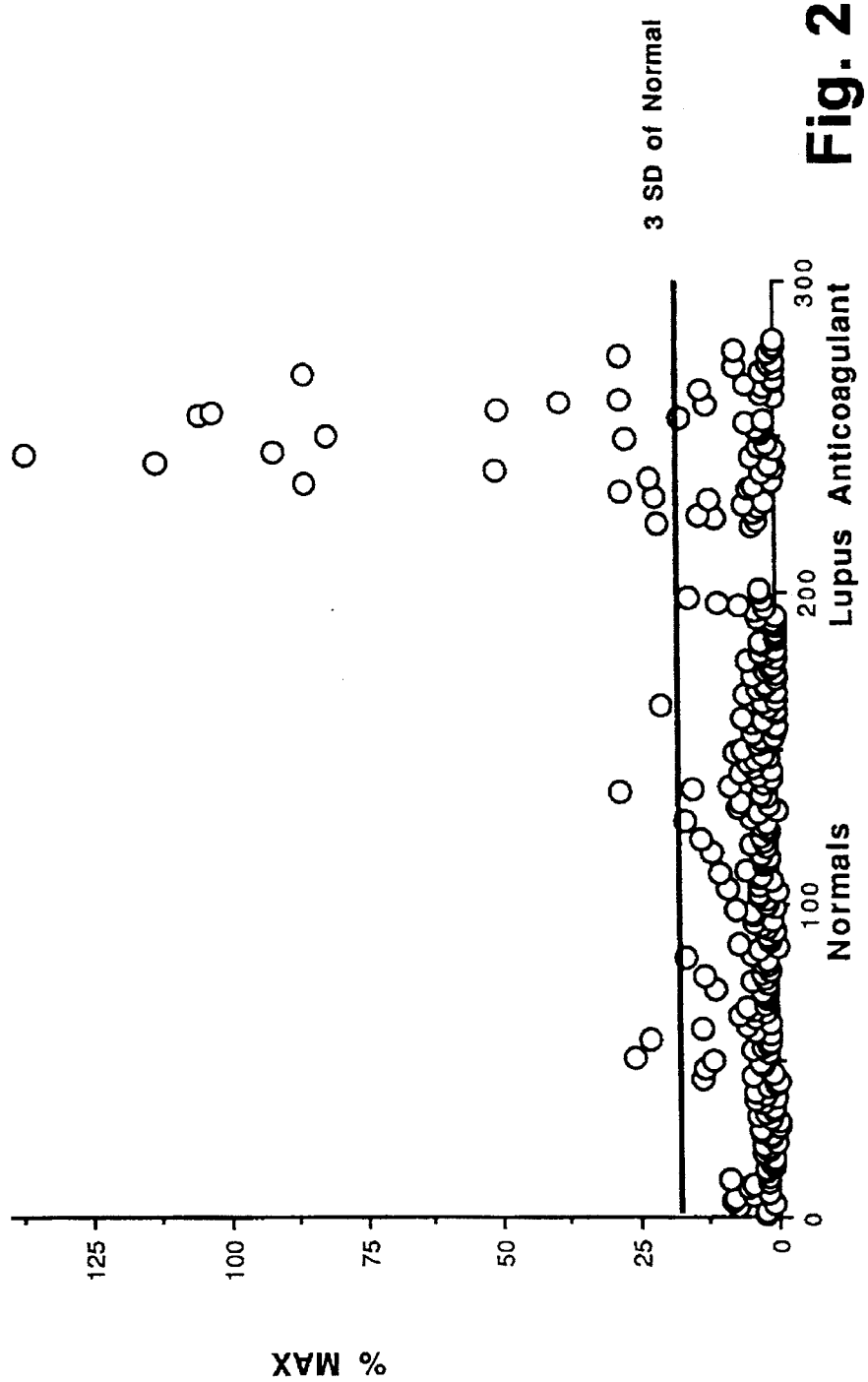
FIG. 2 is a graph depicting the comparative results of the ELISA assays for detecting antibodies to thrombomodulin in normal donor plasma and in plasma taken from patients with lupus anticoagulant.

ELISA Assay for Antibodies to Thrombomodulin Using Plasma from Lupus Anticoagulant Patients The ELISA assay was performed as given in Example 1 using plasma from patients with lupus anticoagulant and the results are given in FIG. 2. Among 61 patients, 18 were found to have significantly elevated values of antibodies to thrombomodulin. These anti-thrombomodulin antibodies did not bind to the EGF 456 thrombomodulin fragment in a similar ELISA assay.

EXAMPLE 3

Figure 3:
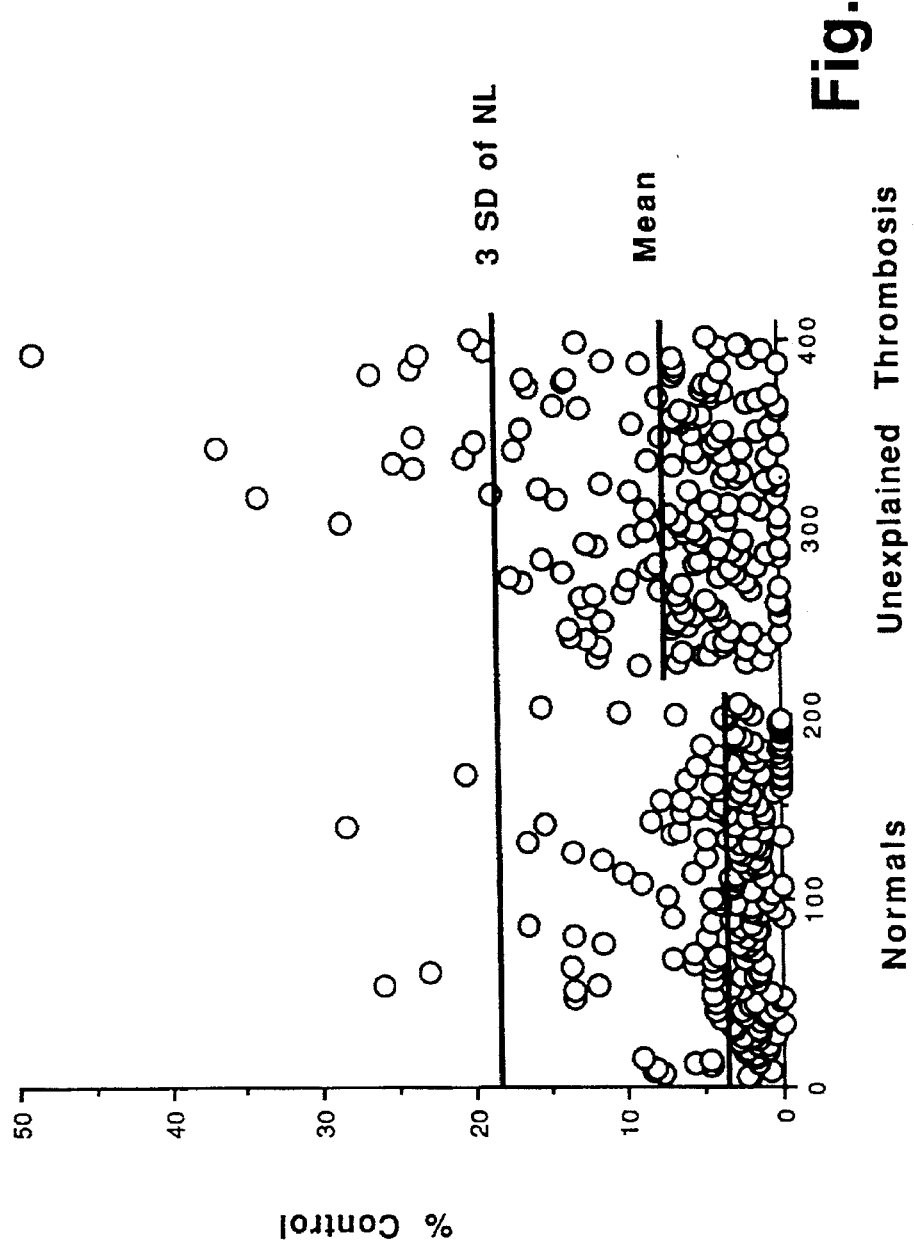
FIG. 3 is a graph depicting the comparative results of the ELISA assays for detecting antibodies to thrombomodulin in normal donor plasma and in plasma taken from patients with unexplained thrombosis.

ELISA Assay for Antibodies to Thrombomodulin Using Plasma from Patients with Unexplained Thrombosis The ELISA assay was performed as given in Example 1 using plasma from patients with unexplained thrombosis, and the results are given in FIG. 3. Among 200 patients, 15 were found to have significantly elevated values of antibodies to thrombomodulin.

EXAMPLE 4

Figure 4:
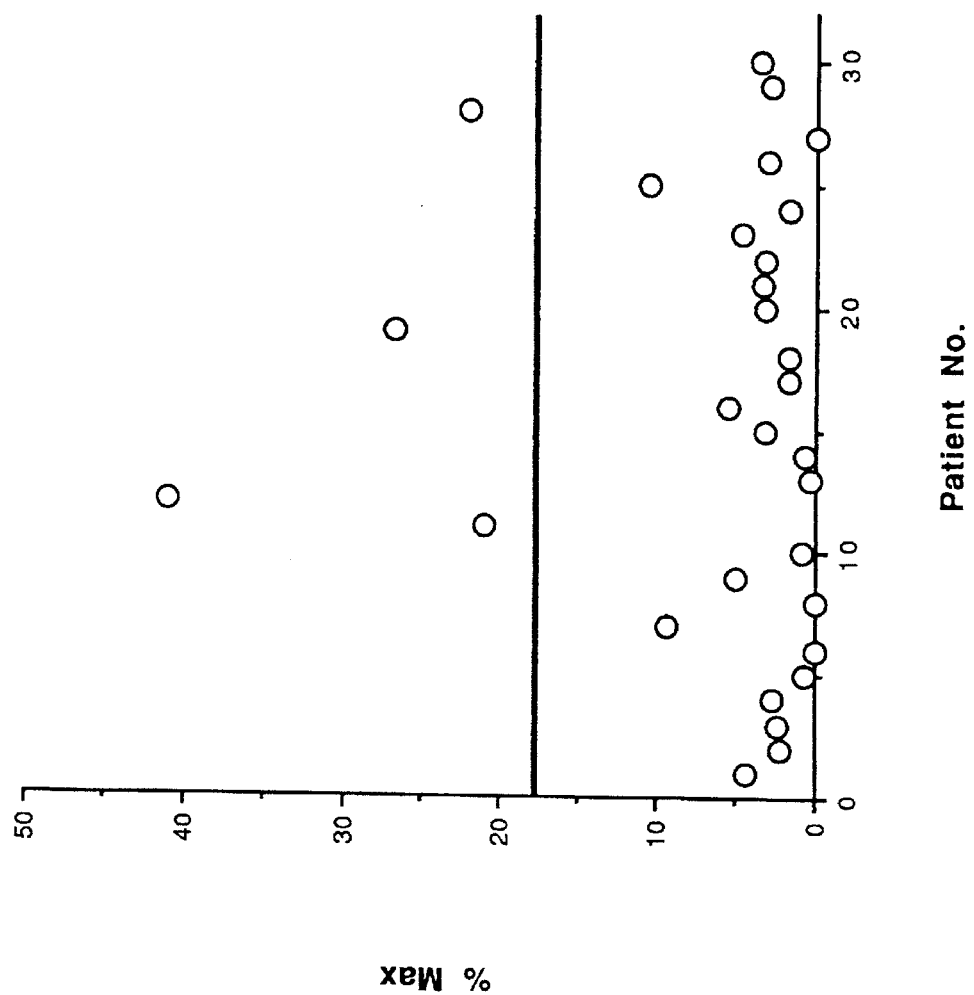
FIG. 4 is a graph depicting the comparative results of the ELISA assays for detecting antibodies to thrombomodulin in normal donor plasma and in plasma taken from patients with premature atherosclerosis and myocardial infarction (MI).

ELISA Assay for Antibodies to Thrombomodulin Using Plasma from Patients Who Experienced Premature Atherosclerosis and Myocardial Infarction The ELISA assay was performed as given in Example 1 using plasma from patients with premature atherosclerosis and myocardial infarction, and the results are given in FIG. 4. Among 30 patients, 4 were found to have significantly elevated values of antibodies to thrombomodulin.

EXAMPLE 5

Figure 5:
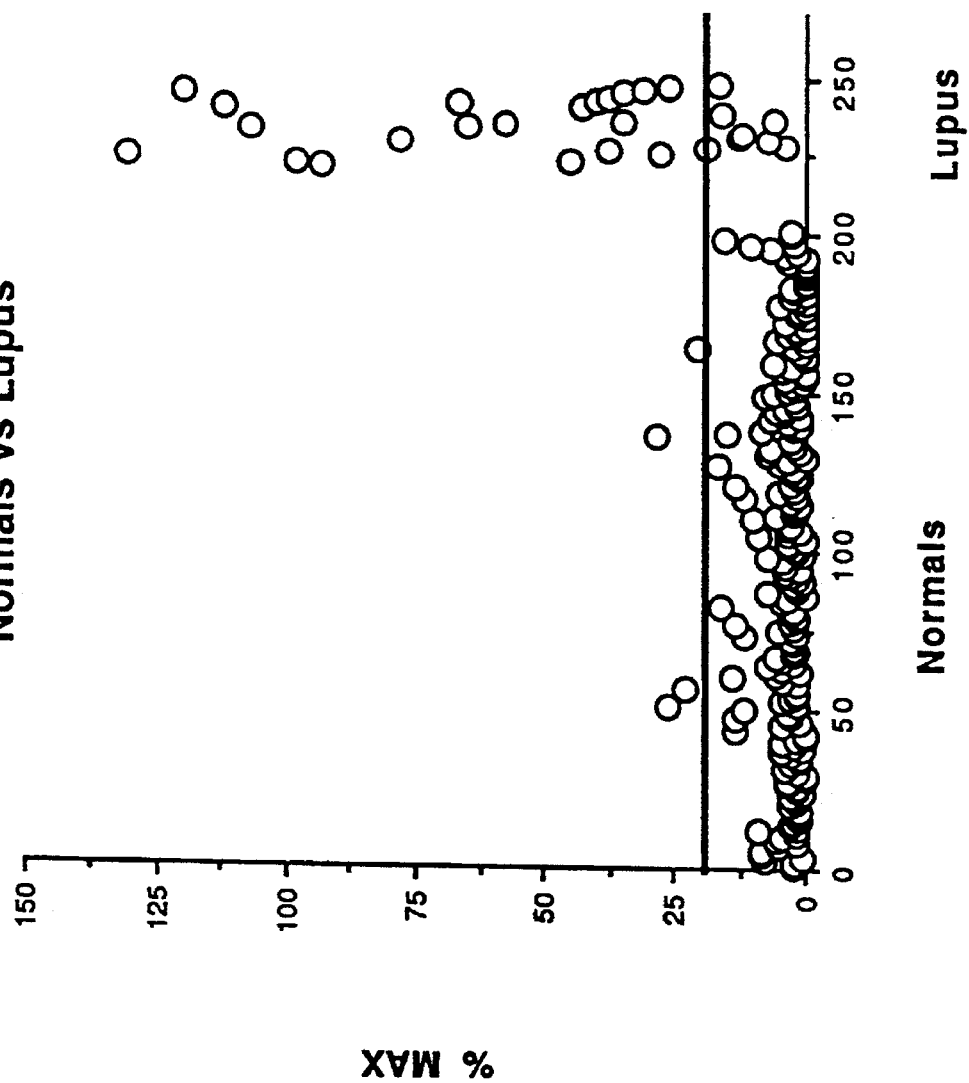
FIG. 5 is a graph depicting the comparative results of the ELISA assays for detecting antibodies to thrombomodulin in normal donor plasma and in plasma taken from patients with systemic lupus erythematosus.

ELISA Assay for Antibodies to Thrombomodulin Using Plasma from Patients with Systemic Lupus Erythematosus The ELISA assay was performed as given in Example 1 using plasma from patients with systemic lupus erythematosus (SLE), and the results are given in FIG. 5. Twenty of twenty-eight patients with SLE demonstrated elevated values of antibodies to thrombomodulin.

EXAMPLE 6

ELISA Assay for Antibodies to Thrombomodulin Using Plasma from Patients with Systemic Lupus Erythematosus and Nephritis The ELISA assay was performed as given in Example 1 using plasma from patients with lupus anticoagulant and nephritis. Among 14 patients with lupus nephritis, 13 were found to have significantly elevated values of antibodies to thrombomodulin. In contrast, of 14 patients with systemic lupus erythematosis but without nephritis, only eight patients demonstrated antibodies to thrombomodulin. Thus, these antibodies indicate a risk factor for nephritis in systemic lupus erythematosis patients. It further illustrates the importance of the Protein C pathway in inflammatory disease as well as thrombotic disease.

The plate-binding ELISA assays described above can also be conducted with fragments of the thrombomodulin molecule. As illustrated in Example 7 below, different populations of antibodies, which may correspond to various disease states, recognize several portions of the whole thrombomodulin molecule. Monitoring changes in the reactivity of antibodies to various fragments of the thrombomodulin molecule may provide information as to the progression of a patient's disease.

EXAMPLE 7

Figure 6:
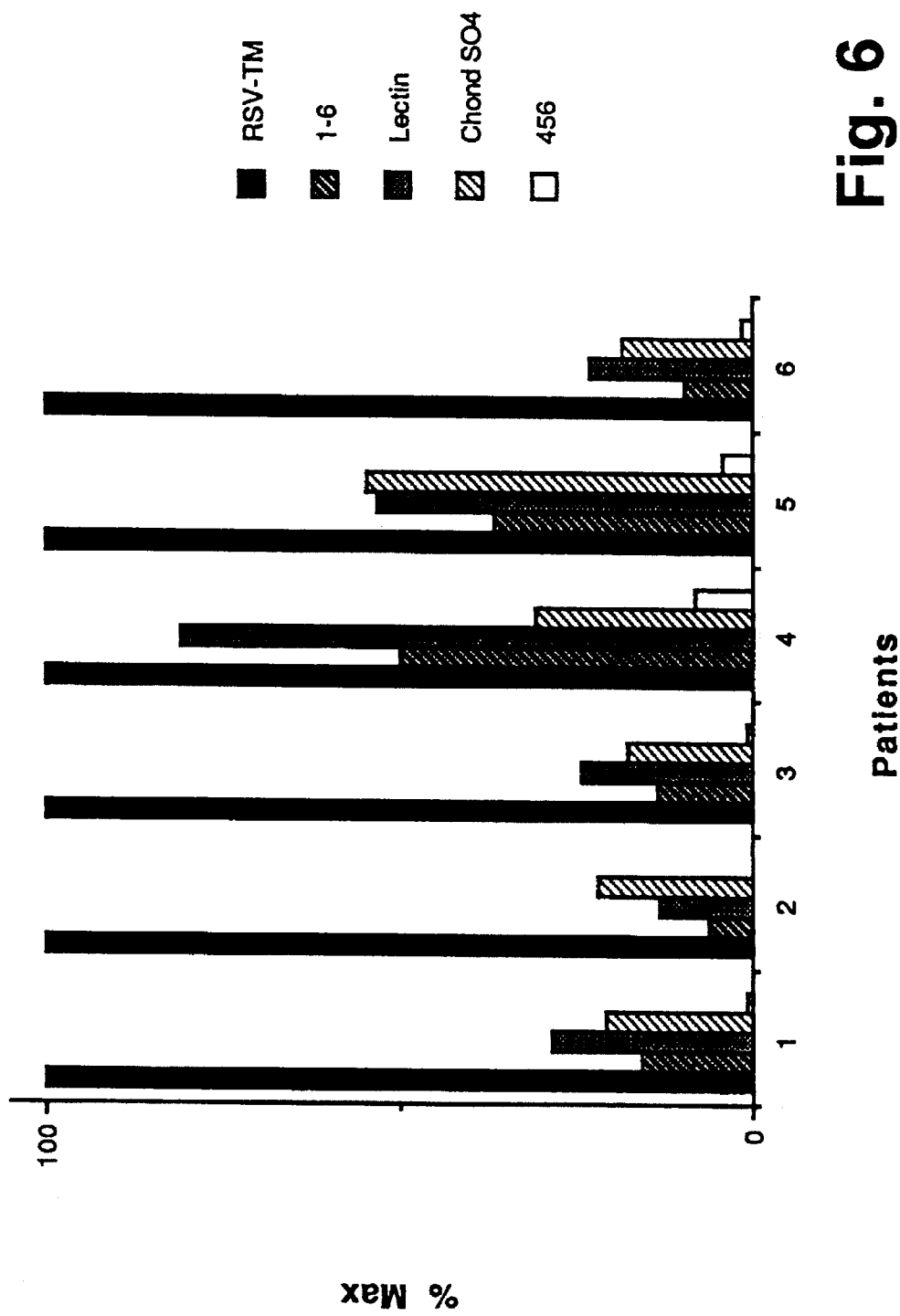
FIG. 6 is a graph depicting the comparative results of the ELISA assays for the TMAB epitope mapping of the recombinant, soluble thrombomodulin (RSV-TM), EGF 1-6 domain (1-6), lectin domain, serine/threonine rich domain containing chondroitin sulfate attachment (chond SO$_4$), and EGF 456 domain (456).

ELISA Assay for Antibodies to Thrombomodulin Fragments Using Normal Donor Plasma The plate-binding ELISA assay described in Example 1 was also conducted for each of the thrombomodulin fragments obtained by expression of the lectin domain (SEQ ID NO:5) encoded by SEQ ID NO:4, EGF 1-6 domain (SEQ ID NO:7) encoded by SEQ ID NO:6, EGF 456 domain (SEQ ID NO:9) encoded by SEQ ID NO:8, and the serine/threonine rich domain containing chondroitin sulfate (SEQ ID NO:11) encoded by SEQ ID NO:10. Reactivity to the whole sTM molecule was used as a control. The microtiter plates were prepared by adding 50 µl of a 10 µg/ml suspension of each fragment in coating buffer to a series of wells. The results of the ELISA assays are depicted in FIG. 6 in a TMAB epitope mapping. Antibodies to thrombomodulin were shown to recognize several portions of the whole thrombomodulin molecule. Reactivity was observed with each thrombomodulin fragment, and an immunodominant epitope was not observed. It is apparent from this epitope mapping that screening for antibodies to thrombomodulin using only one fragment of the thrombomodulin molecule would miss several antibodies. Therefore, while the four thrombomodulin fragments could be used as the plate-binding component in an ELISA assay, sTM would be preferred in a routine assay so as to achieve maximum reactivity in a screening assay. However, it may be desired to categorize the type of antibody found in the patient is blood stream, and this could be done by differential ELISA assays using different thrombomodulin fragments.

EXAMPLE 8

Thrombomodulin Antibody IgG Inhibition of Protein C Activation by Recombinant Soluble Thrombomodulin The ability of thrombomodulin antibody IgG to inhibit soluble thrombomodulint's acceleration of thrombin-dependent Protein C activation was determined using a chromogenic assay.

Patient antibody 30 mg/ml (200 µM) total IgG was added to 4 nM thrombomodulin, providing a 20,000 molar excess of antibody, and incubated overnight (16 h). A 10 µl aliquot was then used to determine thrombomodulin activity in a 70 µl reaction containing 1 µM human Protein C, 120 µM calcium, and 1.2 nM human thrombin which was allowed to proceed for 10 minutes at 37° C. The reaction was terminated, and free thrombin was inhibited by the addition of 10 µl bovine ATIII to a final concentration of 1.8 µM (125 µg/ml). The resulting activated Protein C was determined by its ability to hydrolyze spectrozyme pCa and the resulting rate of para-nitroanalide formed monitored at 405 nM using a kinetic microtiter plate reader. The assay was performed without the addition of patient antibody IgG as a control sample.

Figure 7:
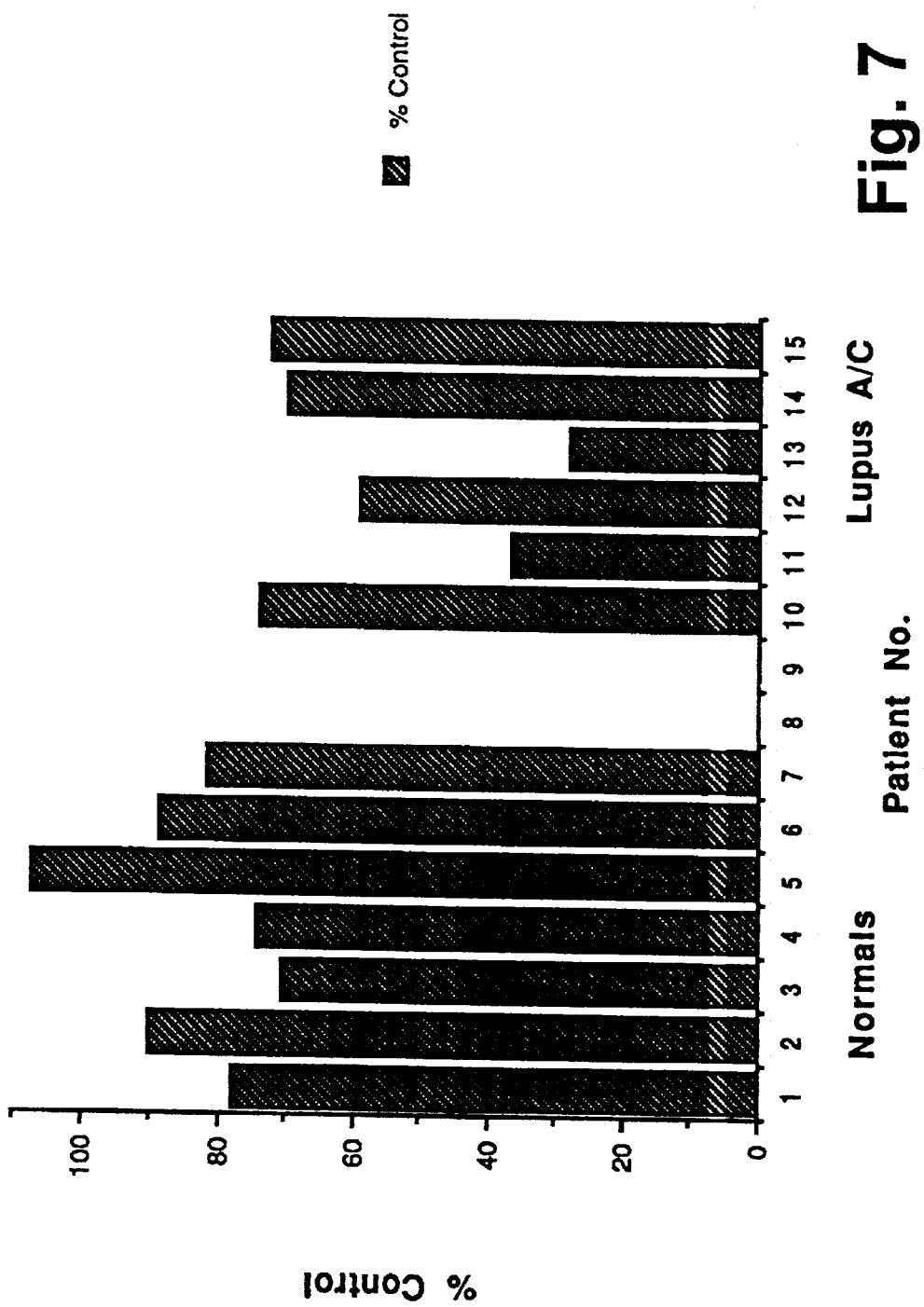
FIG. 7 is a graph depicting the effects of thrombomodulin antibody IgG on the inhibition of Protein C activation by recombinant, soluble thrombomodulin.

As given in FIG. 7, the results are expressed in terms of the amount of activated Protein C obtained in the patient sample as a percent of that obtained in the control sample with no antibody. None of the seven normal controls showed significant inhibition of Protein C activation. In three of six patients, Protein C activation was inhibited by 40%–70% (to 60% to 30% of control).

EXAMPLE 9

Purification Procedures for Recombinant Soluble Thrombomodulin

To purify the protein, the conditioned medium from the human 293 cells producing the recombinant soluble thrombomodulin was harvested. After concentrating from 20 liters to 2 liters (100×) using a 10,000 molecular weight cut off membrane (Amicon, Beverly, Mass.), the concentrated conditioned media is then batch absorbed to 200 ml of QAE (Pharmacia, Uppsala, Sweden) preswollen in 0.02M Tris-HCl, pH 7.5, 0.15M NaCl (TBS), placed into a 2.5 ml×40 cm column, washed with TBS, and batch eluted with 2M NaCl in 0.02M Tris-HCl, pH 7.5. The eluted material was dialyzed extensively versus TBS and 5 mM $CaCl_2$ (TBS-$Ca^{++}$). The dialyzed eluate from QAE was then applied to a thrombin affinity column equilibrated in TBS-$Ca^{++}$. The immobilized thrombin affinity column was prepared by linking bovine thrombin at 5 mg/ml to AffiGel 10 (Bio-Rad Laboratories, Hercules, Calif.) and inactivating the protease with DFP. After loading, the thrombin column is washed with 0.4M NaCl in 0.02M Tris-HCl, pH 7.5, 5 mM $CaCl_2$ and finally eluted with 2M NaCl in 0.02M Tris-HCl, and 1 mM EDTA. The resulting sTM was further fractionated by anion exchange on a Mono-Q column (Pharmacia, Uppsala, Sweden) into a form lacking chondroitin sulfate eluting in low salt (0.45M NaCl) and into a form containing chondroitin sulfate eluting in high salt (1.2M NaCl). The purified protein was then utilized in the ELISA assay.

EXAMPLE 10

TM-lectin, TM1-6, TM456, and TM-CS Protein Purification Procedures

For each HPC-4 modified protein, the conditioned medium from the human 293 cells producing the protein was harvested. After concentrating from 20 liters to 2 liters (100×) using a 10,000 molecular weight cut off membrane (Amicon), the concentrated conditioned media were purified in a single step by immunoaffinity chromatography on a 1.5 ml×20 cm column of immobilized HPC-4 (5 mg/ml) monoclonal antibody coupled to AffiGel 10 (Bio-Rad). The column was washed with 200 ml of a buffer containing 1M NaCl, 0.02% $NaN_3$, 20 mMTris-HCl, pH 7.5, and 1 mM $Ca^{++}$, followed by a 200-ml wash with 0.1M NaCl, 0.02% $NAN_3$, 20 mM Tris-HCl, pH 7.5, and 1 mM $Ca^{++}$. The bound proteins were eluted with a low salt buffer containing 0.1M NaCl, 0.02% $NaN_3$, 20 mM Tris-HCl, pH 7.5, and 5 mM EDTA.

We claim:

1. A method for testing a human patient plasma or serum sample for autoantibodies to truncated soluble thrombomodulin to determine the level of risk of said human patient for thrombosis, comprising the steps of:

(a) providing in a reaction chamber a truncated soluble thrombomodulin reagent, said reagent comprising a protein having an amino acid sequence beginning from amino acid position 1 of SEQ ID NO: 1 and extending to an end amino acid position, said end amino acid position selected so that said reagent is capable of binding to known autoantibodies to thrombomodulin, said reagent lacking the cytoplasmic domain of SEQ ID NO: 1 and a sufficient amount of the transmembrane domain so that said reagent is soluble at a concentration sufficient to bind said autoantibodies which may be present in said sample to said truncated soluble thrombomodulin reagent;

(b) adding said sample to said reaction chamber and incubating for a sufficient time to allow said autoantibodies which may be present in said sample to specifically bind with said truncated soluble thrombomodulin reagent thus forming a bound complex;

(c) separating said bound complex from unbound materials remaining in said reaction chamber;

(d) quantitating said bound complex, and correlating the amount of said bound complex with the amount of said autoantibodies present in said sample;

(e) repeating step (a)–(d) using a standard reference antiserum, said standard reference antiserum prepared from human serum or plasma from lupus patients which contain autoantibodies which bind to the soluble thrombomodulin of SEQ ID NO: 3; and (f) comparing results obtained with said sample to that obtained with said standard reference antiserum, whereby said patient's level of risk for thrombosis is greater or less than that of the patients from which said standard reference antiserum was prepared if said sample's autoantibodies are higher or lower, respectively.

2. A method for monitoring a human patient with lupus anticoagulant for thrombotic risk, comprising the steps of:

(a) providing in a reaction chamber a truncated soluble thrombomodulin reagent, said reagent comprising a protein having an amino acid sequence beginning from amino acid position 1 of SEQ ID NO: 1 and extending to an end amino acid position, said end amino acid position selected so that said reagent is capable of binding to known autoantibodies to thrombomodulin, said reagent lacking the cytoplasmic domain of SEQ ID NO: 1 and a sufficient amount of the transmembrane domain so that said reagent is soluble at a concentration sufficient to bind said autoantibodies which may be present in said patient's plasma or serum sample to said truncated soluble thrombomodulin reagent;

(b) adding a first sample taken at a first collection time to said reaction chamber and incubating for a sufficient time to allow said autoantibodies which may be present in said sample to specifically bind with said truncated soluble thrombomodulin reagent thus forming a bound complex;

(c) separating said bound complex from unbound materials remaining in said reaction chamber;

(d) quantitating said bound complex, and correlating the amount of bound complex with the amount of said autoantibodies bound to said truncated soluble thrombomodulin reagent present in said sample;

(e) repeating step (a)–(d) on a second plasma or serum sample obtained from said patient at a second collection time; and (f) comparing the amount of autoantibodies in said first sample to the amount of autoantibodies in said second sample and if said second sample has fewer autoantibodies than said first sample, concluding that there is a decrease in level of risk for thrombosis and if said second sample has more autoantibodies than said first sample, concluding there is an increase in level of risk for thrombosis.

3. A method for testing a human patient plasma or serum sample for autoantibodies to truncated soluble thrombomodulin as an indication of a propensity for a thrombotic disease or intimation, comprising the steps of:

(a) providing in a reaction chamber a truncated soluble thrombomodulin reagent, said reagent comprising a protein having an amino acid sequence beginning from amino acid position 1 of SEQ ID NO: 1 and extending to an end amino acid position, said end amino acid position selected so that said reagent is capable of binding to known autoantibodies to thrombomodulin, said reagent lacking the cytoplasmic domain of SEQ ID NO: 1 and a sufficient amount of the transmembrane domain so that said reagent is soluble at a concentration sufficient to bind said autoantibodies which may be present in said sample to said truncated soluble thrombomodulin reagent (b) binding said truncated soluble thrombomodulin reagent to the surface of said reaction chamber;

(c) washing said reaction chamber to remove reactants but so that said truncated soluble thrombomodulin reagent remains bound thereto;

(d) adding a blocking buffer protein to said reaction chamber to prevent subsequent nonspecific binding of said autoantibodies and other proteins which may be present in the sample to be tested to said reaction chamber;

(e) washing said reaction chamber to remove reactants but so that said truncated soluble thrombomodulin reagent and said blocking buffer protein remain bound thereto;

(f) adding said sample to said reaction chamber and incubating for a sufficient time to allow said autoantibodies in said sample to specifically bind with said truncated soluble thrombomodulin reagent;

(g) washing said reaction chamber to remove reactants but so that said autoantibodies specifically bound to said truncated soluble thrombomodulin reagent remain bound thereto;

(h) adding a signal generating means to said reaction chamber, said signal generating means capable of binding to said bound autoantibodies to form a detectable end product; and (i) quantitating said detectable end product to determine the amount of said autoantibody, the presence of said autoantibodies indicating said propensity for said thrombotic disease or inflammation.

4. The method according to claim 3, wherein said detectable end product is quantitated by a radioimmunoassay.

5. The method according to claim 3, wherein said detectable end product is quantitated by a colorimetric assay.

6. The method according to claim 5, wherein said colorimetric assay comprises the steps of:

(a) incubating said autoantibodies bound to said truncated soluble thrombomodulin with an enzyme-conjugated anti-human antibody, said enzyme-conjugated anti-human antibody comprising an antibody to specifically bind with said autoantibodies bound to said truncated soluble thrombomodulin, to form an autoantibody-antibody-enzyme complex;

(b) adding an enzyme substrate to said autoantibody-antibody-enzyme complex, said enzyme substrate comprising a chemical substance which reacts with an enzyme portion of said enzyme-conjugated anti-human antibody to form a detectable end product; and (c) quantitating said detectable end product.

7. The method according to claim 3, wherein said colorimetric method comprises the steps of:

(a) incubating said autoantibodies bound to said truncated soluble thrombomodulin with an alkaline phosphatase-conjugated anti-human antibody, said alkaline phosphatase-conjugated anti-human antibody comprising an antibody to specifically bind to said autoantibodies bound to said truncated soluble thrombomodulin, to form an autoantibody-antibody-enzyme complex;

(b) adding an enzyme substrate to said autoantibody-antibody-enzyme complex, said enzyme substrate comprising p-nitrophenyl phosphate which reacts with said alkaline phosphatase-conjugated anti-human antibody to form said end product comprising p-nitrophenol; and (c) quantitating said end product comprising p-nitrophenol.

8. The method according to claim 6 or 7, wherein quantitating said end product is semi-quantitatively determined by visual observation of color intensity.

9. The method according to claim 6 or 7, wherein quantitating said end product is determined using instrumentation for detecting color intensity.

10. The method according to claim 9, wherein said reaction chamber is a microtiter plate well and said instrumentation is an automatic plate reader equipped with spectrophotometric capabilities for monitoring absorbance at a wavelength appropriate to detect said color intensity.

11. The method according to claim 6, wherein the enzyme portion of said enzyme-linked anti-human antibody is selected from the group consisting of alkaline phosphatase, horseradish peroxidase, β-galactosidase, glucose oxidase, β-lactamase, and catalase.

12. A method for monitoring a human patient with lupus anticoagulant for nephritis, comprising the steps of:

(a) providing in a reaction chamber a truncated soluble thrombomodulin reagent, said reagent comprising a protein having an amino acid sequence beginning from amino acid position 1 of SEQ ID NO: 1 and extending to on end amino acid position, said end amino acid position selected so that said reagent is capable of binding to known autoantibodies to thrombomodulin, said reagent lacking the cytoplasmic domain of SEQ ID NO: 1 and a sufficient amount of the transmembrane domain so that said reagent is soluble at a concentration sufficient to bind said autoantibodies which may be present in said patient's serum or plasma to said truncated soluble thrombomodulin reagent;

(b) adding a first sample of said patient's serum or plasma taken at a first collection time to said reaction chamber and incubating for a sufficient time to allow said autoantibodies which may be present in said sample to specifically bind with said truncated soluble thrombomodulin reagent, thus forming a bound complex;

(c) separating said bound complex from unbound materials remaining in said reaction chamber;

(d) quantitating said bound complex, and correlating the amount of said bound complex with the amount of said autoantibodies present in said sample;

(e) repeating step (a)–(d) on a second sample of plasma or serum obtained from said patient at a second collection time; and (f) comparing the amount of said autoantibodies in said first sample to the amount of said autoantibodies in said second sample and if said second sample has fewer autoantibodies than said first sample, concluding that there is a decrease in level of risk for nephritis and if said second sample has more autoantibodies than said first sample, concluding that there is an increase in level of risk for nephritis.

13. A method for testing a human patient plasma or serum sample for autoantibodies to truncated soluble thrombomodulin as an indication of a propensity for a thrombotic disease or intimation, comprising the steps of:

(a) providing in a reaction chamber a truncated soluble thrombomodulin reagent, said reagent comprising a protein having an amino acid sequence beginning from amino acid position 1 of SEQ ID NO: 1 and extending to an end amino acid position, said end amino acid position selected so that said reagent is capable of binding to known autoantibodies to thrombomodulin, said reagent lacking the cytoplasmic domain of SEQ ID NO: 1 and a sufficient amount of the transmembrane domain so that said reagent is soluble at a concentration sufficient to bind said autoantibodies which may be present in said sample to said truncated soluble thrombomodulin reagent;

(b) adding said sample to said reaction chamber and incubating for a sufficient time to allow said autoantibodies which may be present in said sample to specifically bind with said truncated soluble thrombomodulin reagent thus forming a bound complex;

(c) separating said bound complex from unbound materials remaining in said reaction chamber; and (d) quantitating said bound complex, and correlating the amount of said bound complex with the amount of said autoantibodies in said sample, the presence of said autoantibodies indicating said propensity for said thrombotic disease or information.

14. The method of claim 13, wherein said truncated soluble thrombomodulin reagent is a fragment of SEQ ID NO: 1, which fragment is SEQ ID NO:5.

15. The method of claim 13, wherein said truncated soluble thrombomodulin reagent is a fragment of SEQ ID NO:1, which fragment is SEQ ID NO:7.

16. The method of claim 13, wherein said truncated soluble thrombomodulin reagent is a fragment of SEQ ID NO:1, which fragment is SEQ ID NO:9.

17. The method of claim 13, wherein said truncated soluble thrombomodulin reagent is a fragment of SEQ ID NO:1, which fragment is SEQ ID NO:11.

18. The method of claim 13, wherein said truncated soluble thrombomodulin reagent is a fragment of SEQ ID NO:1, which fragment comprises at least one epitope capable of binding an autoantibody to truncated soluble thrombomodulin.

19. The method of claim 13, wherein said truncated soluble thrombomodulin reagent is a fragment of SEQ ID NO:1, which fragment is SEQ ID NO:3.

* * * * *

UNITED STATES PATENT AND TRADEMARK OFFICE
CERTIFICATE OF CORRECTION

PATENT NO. : 5,639,625
DATED : June 17, 1997
INVENTOR(S) : Craig W. Carson and Charles T. Esmon It is certified that error appears in the above-indentified patent and that said Letters Patent is hereby corrected as shown below:

Column 8, line 6, change "7.4%" to --17.4%--.

Column 10, line 62, change "NAN$_3$" to --NaN$_3$--.

Column 33, line 15, Claim 3, change "intimation" to --inflammation--.

Column 33, line 28, Claim 3, after "reagent" insert --;--.

Column 34, line 12, Claim 7, change "claim 3" to --claim 5--.

Column 34, line 13, Claim 7, change "method" to --assay--.

Column 35, line 18, Claim 13, change "intimation" to --inflammation--.

Column 36, line 10, Claim 13, change "information" to --inflammation--.

Signed and Sealed this

Thirty-first Day of March, 1998

*Attest:*

BRUCE LEHMAN

*Attesting Officer*    *Commissioner of Patents and Trademarks*